United States Patent

Mittal et al.

[11] Patent Number: 5,818,731
[45] Date of Patent: Oct. 6, 1998

[54] METHOD AND APPARATUS FOR MEASURING QUALITY OF FRYING/COOKING OIL/FAT

[76] Inventors: Gauri S. Mittal, 12 Briarlea Road, Guelph, Ontario, Canada, N1G 3H5; Satheesh Paul, 1167 Windsor Hill Blvd., Mississauga, Ontario, Canada, L5V 1N9; Gordon L. Hayward, 48 Schweitzer St., Kitchener, Ontario, Canada, N2K 1B4

[21] Appl. No.: 521,291

[22] Filed: Aug. 29, 1995

[51] Int. Cl.[6] .................................................. G01N 21/00
[52] U.S. Cl. ........................................ 364/497; 73/61.41
[58] Field of Search .................................... 364/496, 497, 364/498, 557; 73/31.03, 32 R, 53.01, 53.02, 53.05, 53.06, 53.07, 61.41, 61.43, 61.46–61.48, 61.71, 61.76, 73, 74; 324/658, 659, 663, 664, 665, 672, 679, 686

[56] References Cited

U.S. PATENT DOCUMENTS

| | | |
|---|---|---|
| 2,892,378 | 6/1959 | Canada . |
| 3,526,127 | 9/1970 | Sarkis . |
| 3,739,265 | 6/1973 | Skildum ................................. 324/61 |
| 3,807,860 | 4/1974 | Brainard, II . |
| 3,906,241 | 9/1975 | Thompson . |
| 3,910,702 | 10/1975 | Corll . |
| 4,064,455 | 12/1977 | Hopkins et al. . |
| 4,105,334 | 8/1978 | Halko et al. . |
| 4,198,160 | 4/1980 | Kachel et al. . |
| 4,462,962 | 7/1984 | Baba et al. . |
| 4,470,008 | 9/1984 | Kato ................................ 324/61 R |
| 4,634,881 | 1/1987 | Billion . |
| 4,737,025 | 4/1988 | Steen . |
| 5,028,131 | 7/1991 | Dunsmore . |
| 5,105,085 | 4/1992 | McGuire et al. . |
| 5,194,910 | 3/1993 | Kirkpatrick, Jr. et al. ............. 356/70 |
| 5,239,180 | 8/1993 | Clarke . |
| 5,377,531 | 1/1995 | Gomm .............................. 73/53.05 |

FOREIGN PATENT DOCUMENTS 5180766  7/1993  Japan .

OTHER PUBLICATIONS

Mancini–Filho et al., "Effects of Selected Chemical Treatments on Quality of Fats Used for Deep Frying" JAOCS, v. 63, n. 11, pp. 1452–1456, Nov. 1986.

Pamela J. White, Methods for Measuring Changes in Deep–Fat Frying Oils, *Food Technology*, Feb. 1991, pp. 75–79.

Pei–fen Wu and W.W. Nawar, a Technique for Monitoring the Quality of Used Frying Oils, *JAOCS*, vol. 63, No. 10 Oct. 1986, pp. 1363–1367.

Vincent J. Graziano, Portable Instrument Rapidy Measures Quality of Frying Fat in Food Service Operations, *Food Technology*, Sep. 1979, pp. 54–57.

A.M. Shami, I. Zakl Selm, Dielectic Properties for Monitoring the Quality of Heated Oils, *JAOCS*, vol. 69, No. 9, Sep. 1992, pp. 872–875.

(List continued on next page.)

*Primary Examiner*—Emanuel T. Voeltz
*Assistant Examiner*—M. Kemper

[57] ABSTRACT

A method and apparatus for measuring quality of cooking or frying oil in situ is provided. The oil quality sensor apparatus utilizes simultaneous monitoring of change in the capacitance and optical transmission of the oil in situ in the cooking or frying temperature range. The sensor monitors the chemical degradation as well as the sensory acceptance of the oil. A large, high surface area and multi-plated parallel plate capacitor is used to measure the capacitance to provide a reliable measure of concentration of total polar materials in the high polar region. A diode laser operating at a wavelength of 675 nm and photodetector are used to measure transmittance of the oil in situ with a microprocessor processing the transmittance and capacitance data. The sensor is programmed to indicate oil is to be replaced if either a preset minimum safe percent transmittance threshold is exceeded based on the transmission measurement or a change in capacitance exceeds a preset threshold value.

10 Claims, 21 Drawing Sheets

OTHER PUBLICATIONS

Kuniko Miyagawa, Kazuko Hiral, Tocopherol and Fluorescence Levels in Deep–Frying Oil and Their Measurement for Oil Assessment, *JAOCS*, vol. 68, No. 3, Mar. 1991, pp. 163–166.

M.I. Lima, R.P. Singh, Dynamic Changes in Texture During Frying of French Fries 1993.

S.M. Caladas, F.A.R. Oliviera, Influence of Processing Conditions on Puffer Capacity of Turnips During Acidification 1993.

J. Vijayan, R.P. Singh, Changes in Optical Properties of the Corn Oil During Frying 1993.

M. Gomes da Silva, J. Vijayan, Changes in Viscosity of Corn Oil Subjected to Thermal Degradation 1993.

Plot of Parallel Plate Capacitance Versus Total Polar Materials

Schematic Layout of Indicator Lights and Sensor Controls

Flow Diagram of Microprocessor Program
for Sensor Initialization

Flow Diagram of Microprocessor Program
for Sensor Initialization Continued

Flow Diagram of Microprocessor Program
for Oil Quality Measurement

Flow Diagram of Microprocessor Program
for Oil Quality Measurement Continued

Flow Diagram of Microprocessor Program for Oil Quality Measurement Continued

Flow Diagram of Microprocessor Program for Oil Quality Measurement Continued

Flow Diagram of Microprocessor Program
for Calibration of Temperature Sensor and Capacitor Continued Flow Diagram of Microprocessor Program for Calibration of Optical Circuit

METHOD AND APPARATUS FOR MEASURING QUALITY OF FRYING/COOKING OIL/FAT

FIELD OF THE INVENTION

The present invention relates to a method and apparatus for monitoring the quality of oil and particularly to measuring the quality of frying/cooking oils and fats during cooking by measuring capacitance and transmittance and correlating these with oil degradation.

BACKGROUND OF THE INVENTION

During frying or cooking, the degradation of the frying or cooking oil produces harmful compounds. The oils are exposed to atmospheric oxygen and food moisture at temperatures in the vicinity of 180° C. for extended periods of time during the various cooking processes. As a result, hundreds of chemical reactions take place in the oils thereby producing a significant number of harmful compounds which significantly alter the quality of the oil. Improper monitoring of oil discard times in restaurants poses a public health risk.

Recently, the fast-food industry has begun adopting various methods to maintain the quality and increase the useful life of frying oils. These include the use of active and passive filters, anti-oxidants and better maintenance of fryer equipment. While these methods may improve the quality and life of the oil to some extent, the oil will still continue to degrade until it is unsafe to use. Moreover, the food products absorb large quantities of degraded oil, see BLUMENTHAL, M. M. 1991, A New Look At the Chemistry and Physics of Deep-Fat Frying, Food Technology, 45(2), pp 68–94; and research has proven that excess consumption of degraded oil is unhealthy, as disclosed in CLARK, W. L. and SERBIA, G. W., 1991, Safety Aspects of Frying Fats and Oils, Food Technology, 45(2), pp 84–94. Consequently, the frying or cooking oil must be discarded after a certain amount of use. In many instances oil quality is assessed based on visual inspection wherein for example the cook employs experience to decide when to change the oil based on color, odor, excessive foaming, smoking and by tasting the food products. These are not reliable methods because of their subjective nature.

There are several commercially available tests for rapid measurement of oil quality. These include the RAU-Test also known as the Oxifrit-Test. This is a calorimetric test comprising redox indicators which react with the oxidized compounds in the sample. The color developed is compared against a standard color. Other calorimetric tests are also available but the main drawback to these methods is that they monitor only one aspect of the oil quality.

A sensor produced by Northern Instruments Corp., known as the Foodoil-Sensor™ Oil Quality Analyzer (FOS) measures change in dielectric constant of the cooking oil. Drawbacks of the instrument are that it has to be calibrated against a reference liquid before every measurement. The fresh oil cannot be used as a reference, as every batch of fresh oil contains small, but varying amounts of total polar materials. A reference liquid supplied by the manufacturer corresponding to an FOS reading of 'zero' is also not reliable as the FOS readings show poor correlation in the low polar region. Further, the dielectric constant of hydrocarbons is a function of temperature. The temperature of the oil in a fryer during use is typically in the range of 160° to 180° C. while the ideal operating temperature of the FOS is about 63° C. Therefore, the oil sample from the fryer should be cooled to 63° C., first, to ensure an accurate measurement. This adds to the operational inconvenience and measurement time.

The inadequacy of monitoring any single property of the oil to measure the overall frying oil quality has been pointed out by many researchers; for example, in WU, P. and NAWAR, W. W. 1986; A Technique for Monitoring the Quality of Used Frying Oils; Journal of American Oil Chemists' Society 63(10); pp 1363–1367; and MIYAGAWA, K., HIRAI, K. and TAKEZOE, R. 1991; Tocopherol and Fluorescence Levels in Deep-Frying Oil and Their Measurement for Oil Assessment; Journal of American Oil Chemists' Society 68(3); pp 163–166.

There have been attempts to provide a methodology for measuring oil quality based on measurement of more than one property. For example, it has been disclosed in JACOBSON, G. A., 1991; Quality Control in Deep-Fat Frying Operations; Food Technology, 45(2); pp 72–74; that the measurement of free fatty acids and color can provide a fairly good overall estimate of the frying oil quality. However, measurement of free fatty acids is not a reliable test of overall oil quality.

Wu et al. suggested that the ratio of polymer/FOS reading is a reliable measure of oil quality and combined measurements of viscosity and parallel plate capacitance to obtain this ratio. Drawbacks to this method are that the ratio of polymers/FOS reading declined after the seventh day so that this ratio is misleading beyond this period of time. Another drawback is that a simple and reliable method of measuring the polymer concentration in the oil is unavailable. Ultrasonic methods to measure the change in viscosity of the oil are known as disclosed in LACEY, R. L. and PAYNE, F. A. 1991; Ultrasonic Properties of Frying Oil as a Measure of Viscosity; American Society of Agricultural Engineers; Paper No. 91-6518. ASAE, St. Joseph, Mich., p 16; however, complex and expensive instruments are required. Vijayan et al. have reported correlations between viscosity and absorbance, see VIJAYAN, J., SINGH, R. P. and SLAUGHTER, D. 1993; Changes in Optical Properties of the Corn Oil During Frying; Annual Meeting/Book of Abstracts; Institute of Food Technologists, Chicago, p 229. However, measurement of absorbance at different wavelengths are needed depending on the food to oil ratio.

It has been reported that the color of the frying oil is one of the major parameters of acceptance to be evaluated on a daily basis, see ORTHOEFER, F. T. 1988; Care of Food Service Frying Oils; Journal of American Oil Chemists' Society 65(9); pp 1417–1419. Further, MORTON, I. D. and CHIDLEY, J. E. 1988; Methods and Equipment in Frying; In: Frying of Food, Principles, Changes, New Approaches; Eds. Varela, G., Bender, A. E. and Morton, I. D. Ellis Horwood, Chichester, England; pp 37–51; listed color as the most important factor of oil quality assessment. Regulations in a number of nations stipulate that color must be used as a criterion for discarding frying oils. The Manufacturing Processes Inspection Regulations published by the United States Department of Agriculture [USDA] states that darkened color is an evidence of unsuitability of the frying oil and requires rejection of the oil [Section 3.2.8, USDA, 1985]. Moreover, the color development is an indication of formation of carbonyl compounds in the oil in addition to oxidation and polymerization processes taking place.

In practice the color of cooking oil becomes unacceptable before either the flavor or odor become unacceptable suggesting that the monitoring of color is of more practical importance than the sensing of flavor or odor. A change of color is also a quantifiable property at any given wavelength while taste and odor are highly subjective depending on the person doing the testing. Thus, monitoring of color is an important method for assessing the acceptability of cooking oils.

Therefore, there has been a need for a method and apparatus for in situ monitoring of oil quality which provides a reliable measure of changes in the concentration of total polar materials in addition to optical properties and enables decisions with respect to oil quality to be based on changes in both properties.

SUMMARY OF THE INVENTION

It is an object of the present invention to provide a method and apparatus for in situ testing of frying or cooking oils and fats which is safe and economical and may be routinely used in restaurants.

It is another object of the present invention to provide a method and apparatus which monitors in situ both transmittance of cooking oil in an effective wavelength region and capacitance of the oil and which provides an assessment of the oil based on these properties.

There is provided a method and apparatus for monitoring cooking oil which comprises the simultaneous measurement of change in the capacitance and optical properties of the frying oil to indicate the chemical degradation and sensory acceptance of the oil.

In one aspect of the invention there is provided a device for monitoring change in oil quality comprising a housing having a chamber and an opening for access to the chamber. A multi-plated parallel plate capacitor and a means for measuring transmittance of oil are located in the chamber. Provided is means for measuring the temperature of oil in the chamber. A microprocessor is connected to the capacitor, transmittance measuring means and temperature sensing means to store outputs from these components. The microprocessor calculates transmittance and capacitance of the oil and compares the transmittance value to a reference transmittance value for the oil, and compares the capacitance value to a reference capacitance value and relates changes to an increase in the amount of polar molecular constituents of the oil relative to a reference concentration of polar molecular constituents. The microprocessor correlates the changes in the capacitance and transmittance values using an effective correlation algorithm and provides an output indicative of the quality of the oil. In this aspect of the invention the parallel plate capacitor has a plurality of plates.

In another aspect of the invention there is provided a method for monitoring change in cooking oil quality. The method comprises the steps of measuring values of capacitance, temperature and transmittance of oil in a confined volume in a preselected temperature range; comparing the transmittance value to a reference transmittance value for the oil, comparing the capacitive impedance value to a reference capacitance value and relating changes in the capacitance to an increase in the amount of polar molecular constituents of the oil relative to a reference concentration of polar molecular constituents; and correlating the changes in the capacitance and transmittance values using an effective correlation algorithm and providing an output based on the correlation indicative of the quality of the oil.

BRIEF DESCRIPTION OF THE DRAWINGS

The method and apparatus for measuring in situ oil quality in accordance with the present invention will now be described, by example only, reference being had to the accompanying drawings, in which.

DETAILED DESCRIPTION OF THE INVENTION

Figure 1:
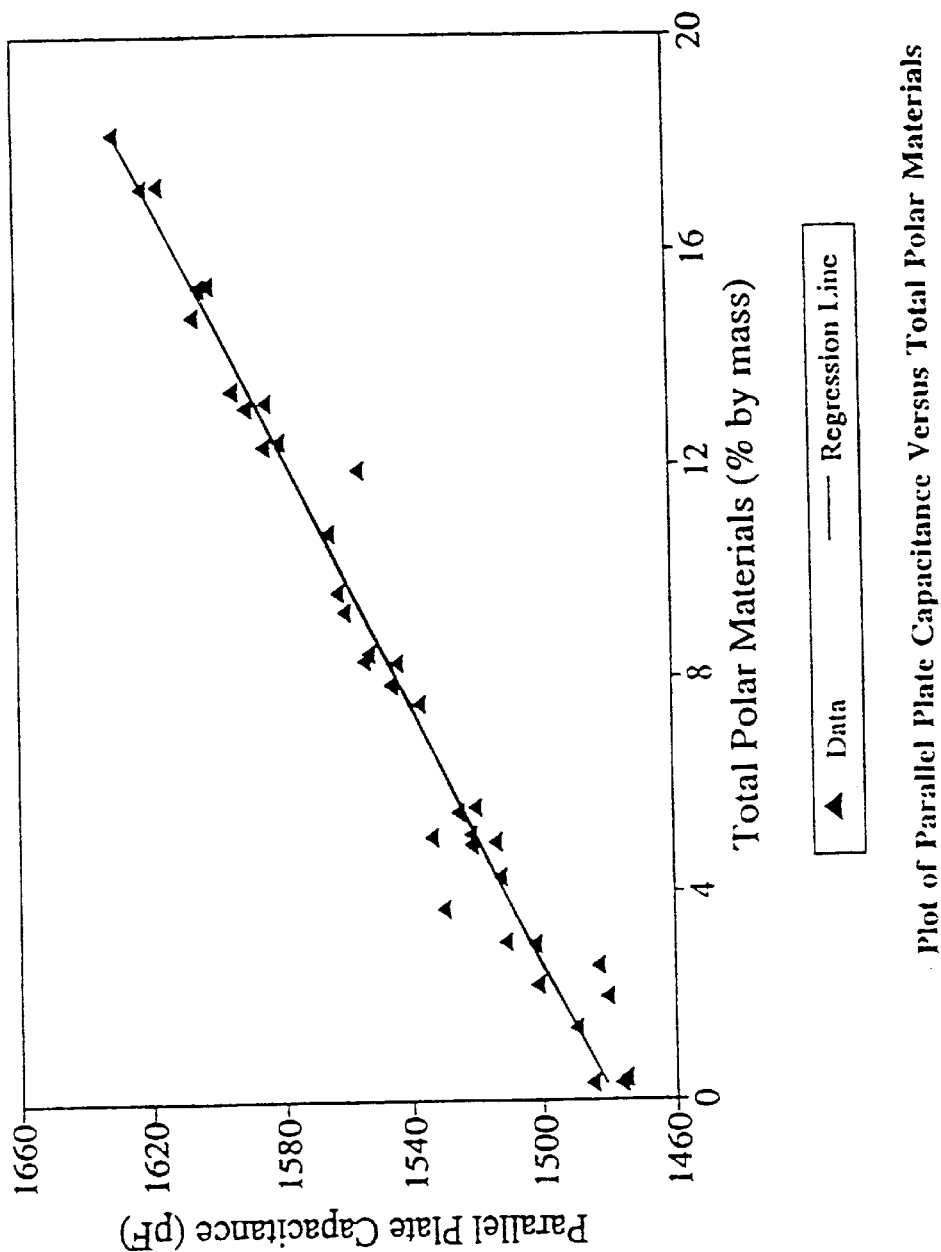
FIG. 1 is a plot of parallel plate capacitance versus total polar materials based on studies by the inventors.

The inventors have conducted extensive studies into the most efficient and comprehensive method of monitoring the quality of cooking oil in situ. It will be understood that cooking oil as used herein refers to frying oils as well oils used in other cooking methods in addition to liquefied hydrocarbon based fats used in cooking/frying applications. They have found that a method much improved over the known art comprises simultaneously monitoring changes in optical transmission and capacitance from which the quality of the cooking oil is determined. A sensor constructed in accordance with the invention has been found to be a good indicator of sensory acceptance of the oil as well as of chemical degradation. Thus, the method and device for monitoring cooking oil forming the present invention comprise measurement of the change of both optical and electrical properties of the cooking oil during use. The methodology employing both these measuring techniques will first be discussed followed by a description of preferred embodiments of a sensor using both techniques.

Capacitance Studies

The results of studies by the inventors show that the quantification of total polar materials is the most reliable method to determine the overall chemical degradation taking place in the oil. The dielectric constant is the only property of the oil that showed high correlation with the concentration of total polar materials, independent of the types of food fried. Therefore, the measurement of capacitance as a means of measuring changes in dielectric constant was found to be the simplest and most accurate method to quantify the total polar materials formed in the oil.

A large parallel plate capacitor with a plurality of parallel plates was advantageously found to be a suitable sensor to measure the change in dielectric constant of the oil. The following assumptions were made to develop a suitable instrumentation system.

1. It is the change in dielectric constant that represents the increase in total polar materials, and not its absolute value.
2. A 100% pure cooking oil contains only non-polar triglycerides and hence any change in the dielectric constant of the pure oil is assumed to be attributed to the total polar materials form during use.

Based on these assumptions the change in dielectric constant is the difference between the measured dielectric constant (which varies with use) and the dielectric constant of the 100% pure oil (which is constant). The equation for the increase in dielectric constant can be generalized as follows:

$$\Delta Kn = Kn_{measured} - Kn_{pure} \quad (1)$$

where n denotes the type of the oil. For a given parallel plate capacitor of fixed geometry and dimensions, this equation can also be expressed as following:

$$\Delta Cn = Cn_{measured} - Cn_{pure} \quad (2)$$

where C denotes the capacitance and the other symbols have the same meaning as in equation (1).

Parallel plate capacitance is a function of the temperature of the oil. Therefore, the measurements are preferably taken at a constant temperature to standardize the results. Measurements are taken at the frying temperature to minimize the measurement time. The regression equation of the temperature-capacitance response of the oil in the frying range of about 155° C. to 185° C., can be stored in the EAPROM of the microprocessor. Once the capacitance and the corresponding oil temperature within this range is measured, the regression equation can be recalled to calculate the capacitance corrected to a standard temperature of measurement.

The temperature-capacitance response of oils may vary slightly, also as a function of the concentration of total polar materials. In such cases, the regression equation for the temperature-capacitance response at the highest permissible concentration of total polar materials is preferably used for standardization. In situations where different oils are used for frying, an operator can recall the proper regression equation by operating an oil selector knob to be discussed below.

The standardized equation (corrected to the standard temperature of measurement) for the increase in dielectric constant can be denoted as follows:

$$\Delta Cn^* = Cn^*_{measured} - Cn^*_{pure} \quad (3)$$

The $Cn^*_{pure}$ of various cooking oils/fats are preferably stored in the EAPROM of the microprocessor and selected by adjustment of a selector switch when programming the sensor for a particular cooking or frying application. For special oils/fats, $Cn^*_{pure}$ values are calculated by the operator and stored in the EPROM of the microprocessor.

FIG. 1 shows the line of best fit for the plot of parallel plate capacitance against total polar materials of a particular fat/shortening based on studies performed by the inventors. For discussion, let 17% by mass of total polar materials be the discarding criteria for that oil. This percentage corresponds approximately to a parallel plate capacitance of 1618 pF. It will be understood that there is a potential for error in categorizing any oil with capacitance less than 1618 pF is good and that with a capacitance above 1618 pF as bad, due to statistical error inherent in regression analysis.

Figure 2:
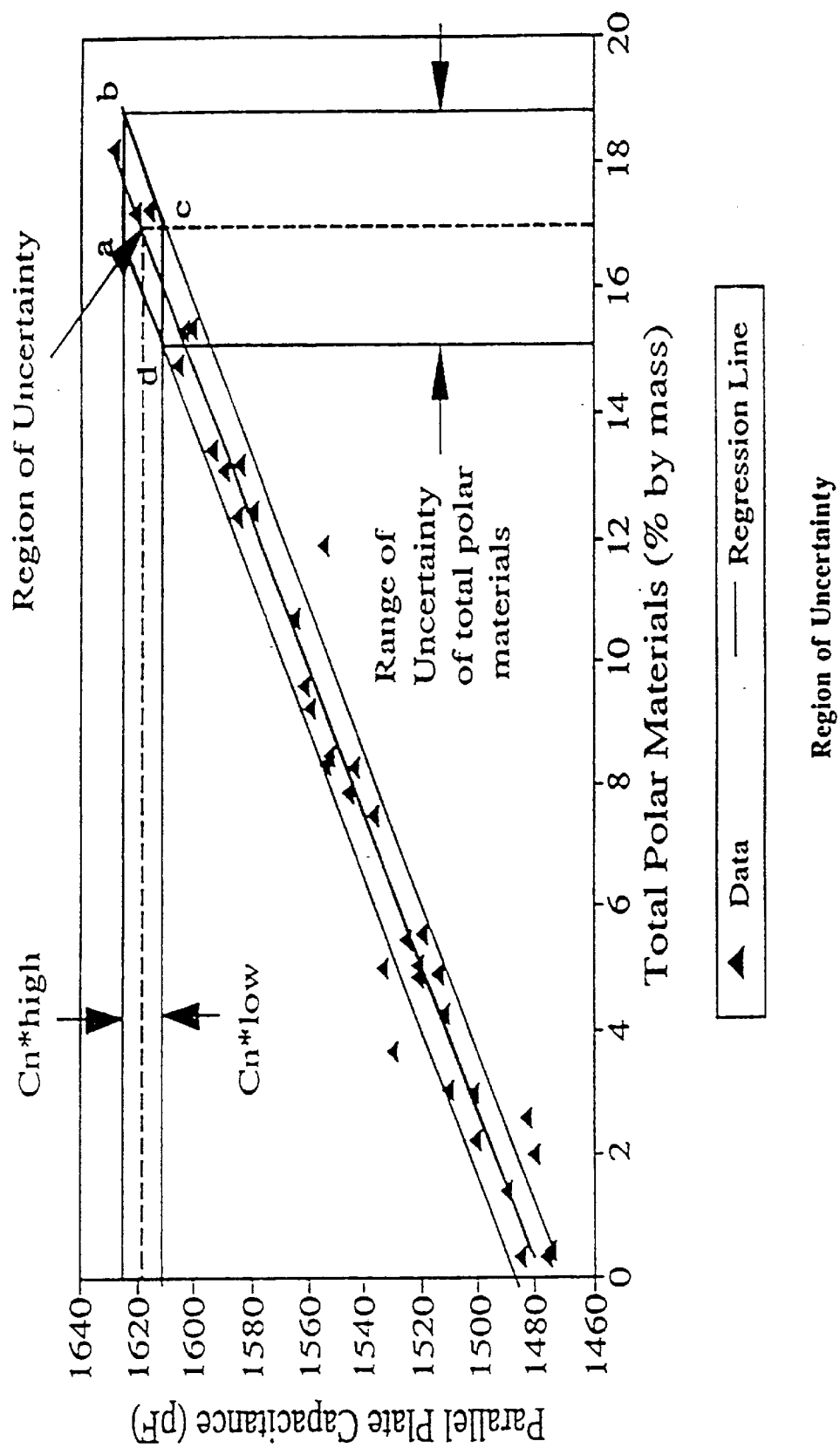
FIG. 2 is the plot of parallel plate capacitance versus total polar materials of FIG. 1 showing a region of uncertainty.

FIG. 2 shows two marginal parallel lines drawn below and above the regression line of FIG. 1. The bottom line defines a lower limit and the upper line defines an upper limit for capacitance. Most of the data points in the high polar material region lie within this narrow band. Therefore, based on these data there is a high probability that the oil with capacitance lower than the lower limit is 'definitely safe' and that with a capacitance higher than the upper limit is 'definitely unsafe'.

This concept gives a small region of uncertainty denoted by the areas defined by points abcd in FIG. 2 in which the probability for an oil to be good or bad is approximately equal. The quality of any oil falling within this region is uncertain, which is represented by a yellow indicator light 122' of the sensor shown in FIG. 7. The upper and lower values of $\Delta Cn^*$ for the region of uncertainty can be denoted as $\Delta Cn^*_{high}$ and $\Delta Cn^*_{low}$, respectively. Therefore, the standardized sensing expression for the concentration of total polar materials present in a frying oil to be good is:

$$Cn^*_{measured} - Cn^*_{pure} \leq \Delta Cn^*_{low} \quad (4)$$

Similarly, the expression for oil considered substandard is:

$$Cn^*_{measured} - Cn^*_{pure} \geq \Delta Cn^*_{high} \quad (5)$$

The $\Delta Cn^*_{high}$ and $\Delta Cn^*_{low}$ of various cooking oils/fats are preferably stored in the EAPROM of the microprocessor for recall during comparison to the measured values.

Optical Measurements

The oils nearing the discarding time should have a higher percent transmittance, in order to develop a sensitive sensor. Studies by the inventors demonstrate that highly degraded and darkened oil samples showed higher percent transmittance in the range of about 645–695 nm, which is the orange red region of the visible spectrum. Therefore, the preferred wavelength of color measurement is in the range 645–695 nm. The transmittance at any wavelength in this range is a good measure of both the orange-red and the darkening color components of the oil. From this range, 675 nm is the most preferred wavelength of color measurement due to the availability of a low cost commercial diode laser at that wavelength.

The optical measurement relies upon measuring the percent transmittance of the oil at 675 nm using a diode laser as the light source and a photodiode as the sensor. Those skilled in the art will understand that other laser/wavelengths may be used. The specific combination of a particular oil and a particular food product will have a specific minimum safe percent transmittance (MSPT) for the oil, below which the oil is bad. The condition that the {difference between measured percent transmittance (variable) of the oil and the minimum safe percent transmittance (constant) estimated for that specific combination} $\geq 0$ must be satisfied for the oil to be considered good and therefore still usable. This expression can be denoted as $(Tn_{measured} - MSPTn) \geq 0$, where T is the percent transmittance and n is oil type. There is no region of uncertainty in the sensing of MSPT.

The minimum safe percent transmittance (MSPT) required by frying oil to be good, depends mainly on the type of the oil used, the type of the food product fried, the application of adsorbents and the taste of customers. The color of food after being cooked in oil is related to the color of the oil. The sensory evaluation of color is unique for each oil and hence the estimation of the MSPT is a function of the oil type. The acceptance limit of color can vary depending on geography, culture, etc. For example, some nationalities prefer french fries very light in color while others are more accustomed to much darker colors. Thus, MSPT of an oil used for frying french fries in some countries may be lower than that in others.

The food product fried is the most important factor that decides the MSPT for an oil. The acceptance limit of color of each food product is different. This can vary also depending on the type of restaurants. For a restaurant operating in a specific nation or geographic location, the MSPT values should be estimated for the combinations of different oils and food products.

Another important factor that influences the estimation of the MSPT is the concentration of animal fats leaching into the oil. A relation between the increase in concentration of leaching fat and the decrease in transmittance should be derived, for various combinations of the oil and the food product. The extent of harmful effects of different animal fats may also vary depending on a wide variety of factors such as cholesterol content. All such parameters should be considered while estimating the MSPT for the safe concentration of leaching fat. The higher value among the MSPT estimated for the sensory acceptance of color and that for the safe concentration of leaching fat, should be accepted as the MSPT for each of the oil-food combination. The present sensor is provided with a food product selection knob for programming in relevant values. An operator can recall the correct MSPTn as a function of food product.

Another important factor influencing the estimation of MSPT is the use of color adsorbent materials while filtering the oil. The adsorbents can increase the transmittance to a certain extent. This also increases the useful life of the oil in terms of sensory acceptance. To estimate the correct MSPT in such cases, a correction factor proportional to both the performance of the adsorbents and the extent of the adsorbent application should be subtracted from the uncorrected MSPT.

In frying, the extent of the application of adsorbents may vary depending on a number of factors, such as the quality and quantity of adsorbent used, frequency of application, etc. Therefore, the sensor is provided with an adsorbent selector knob to recall the correct MSPTn* as a function of the extent of the application of adsorbents.

The standardized MSPTn values for various combinations of oil type, food product and the extent of adsorbent application are stored in the EAPROM of the microprocessor. By operating the oil selector, food product selector and the adsorbent selector switches, any of the above combinations may be identified and an appropriate MSPTn* recalled for sensing.

A sample truth table is given in Table 1, for the selector knobs to recall the correct $Cn^*_{pure}$, $\Delta Cn^*_{low}$, $\Delta Cn^*_{high}$ and MSPTn* values from the EAPROM, for the combinations between two frying oils, two food products and two states of adsorbent application. As $Cn^*_{pure}$ depends only on the oil type, $C^*_{110\ pure} = C^*_{121\ pure}$ and $C^*_{210\ pure} = C^*{221}_{pure}$.

Transmittance is also a function of the temperature of the oil. Therefore, the transmittance measured at any temperature has to be corrected for the standard temperature of measurements. The standardization method is similar to one used for the capacitance. The regression equations of the temperature-transmittance response of various frying oils in the range of about 155° to about 185° C. are stored in the EAPROM of the microprocessor. Once the temperature and the corresponding transmittance of the oil within this range are measured, the regression equation can be recalled to calculate the transmittance corrected to the standard temperature of measurement. The operator can recall the proper regression equation by using the oil selector knob to be discussed below.

The standardized sensing expression for the color (corrected to the standard temperature of measurement) of a frying oil to be good is:

$$(Tn^*_{measured} - MSPTn^*) \geq 0.$$

Design of Oil Quality Sensor

Figure 3:
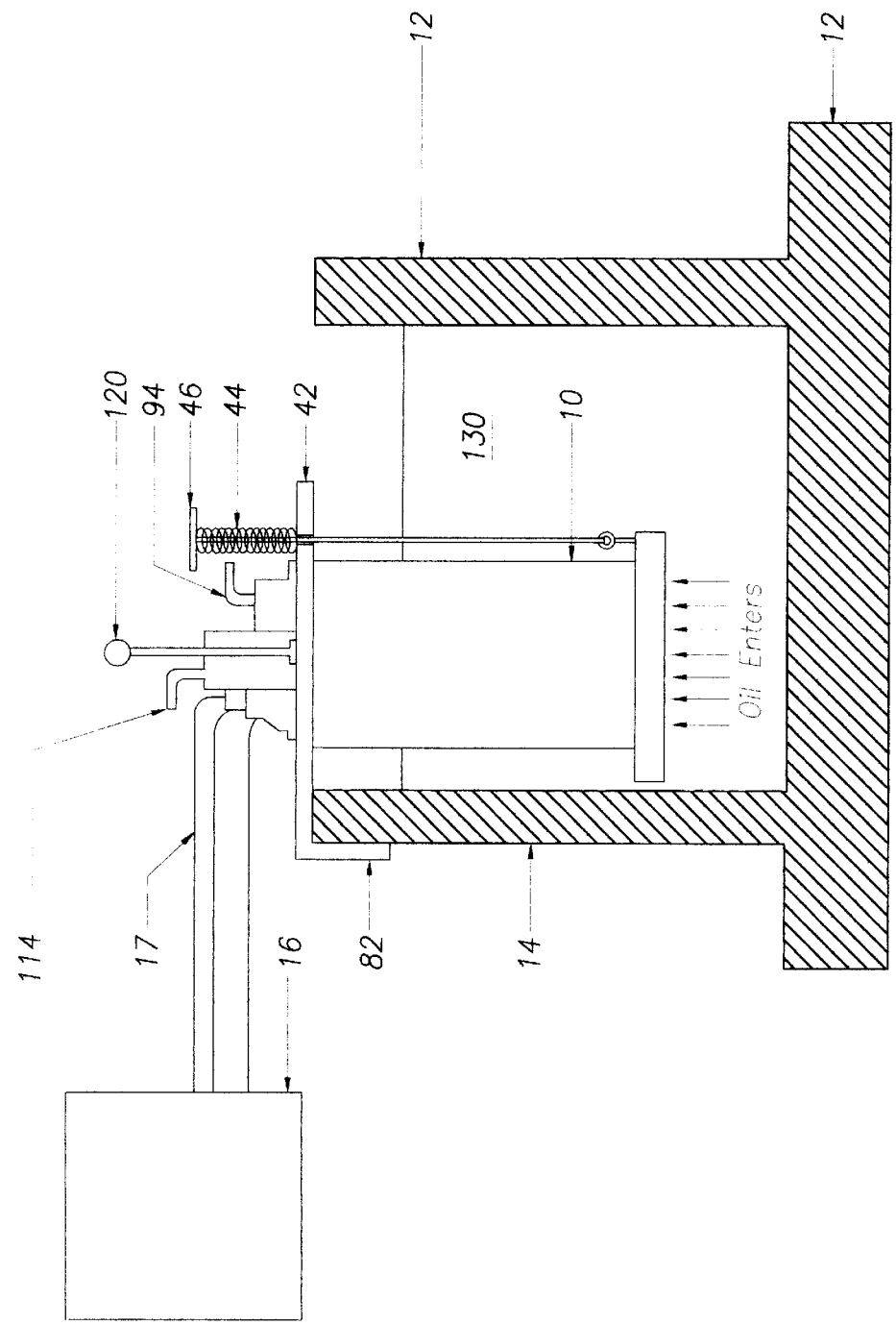
FIG. 3 is a cross sectional view of a conventional fryer with a sensor for monitoring cooking oil quality, constructed in accordance with the present invention, suspended in the interior of the fryer.

Referring first to FIG. 3, a cooking oil sensor constructed in accordance with a preferred embodiment of the present invention is shown generally at 10 inserted into a fryer 12 and hanging from fryer wall 14. Sensor 10 includes a microprocessor 16 connected by a wire bus 17 with capacitance measuring means, temperature sensing means and means for measuring optical properties of the oils to be discussed hereinafter.

Figure 4:
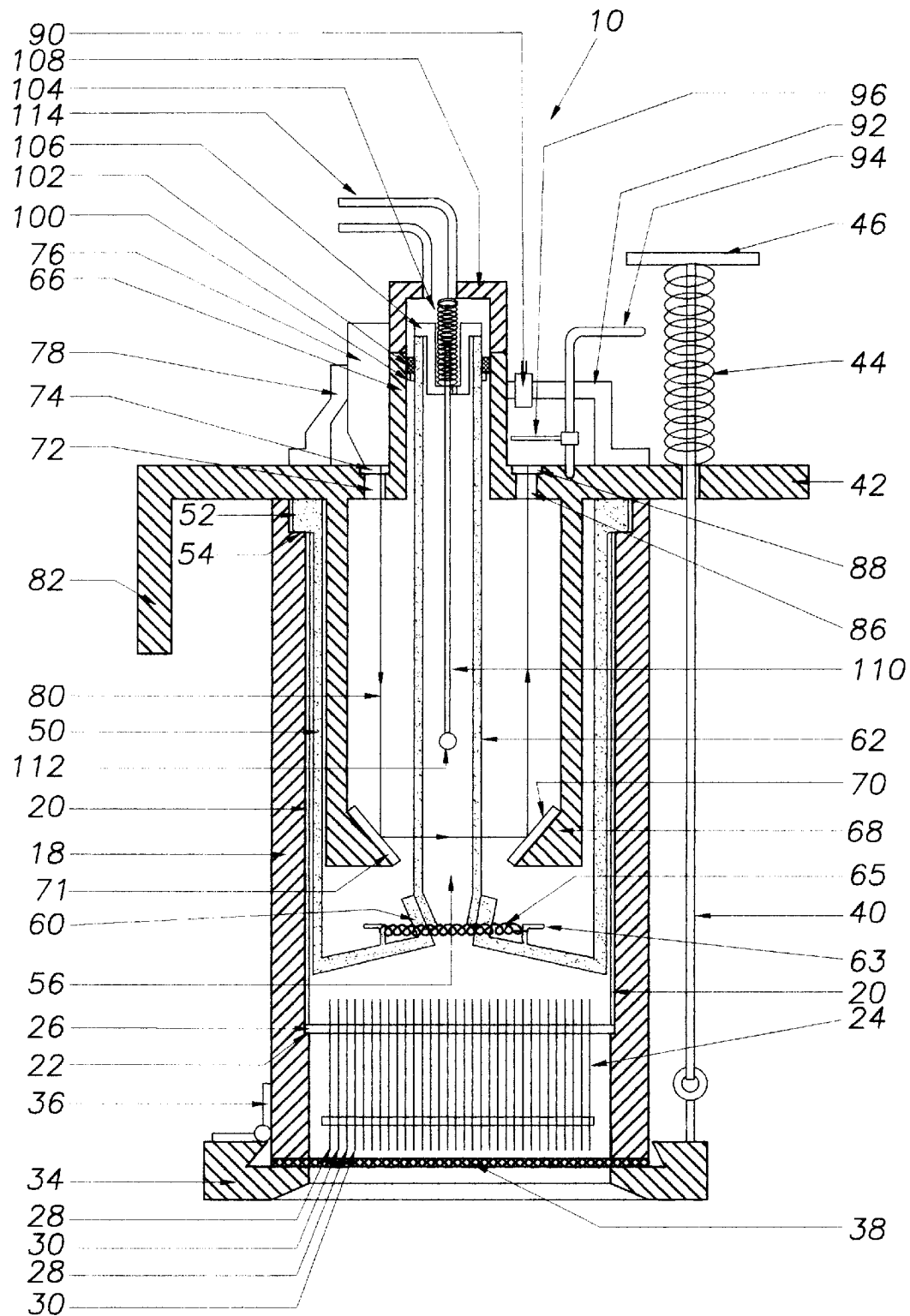
FIG. 4 is a cross sectional view of a sensor for measuring cooking oil quality in accordance with the present invention.
Figure 5:
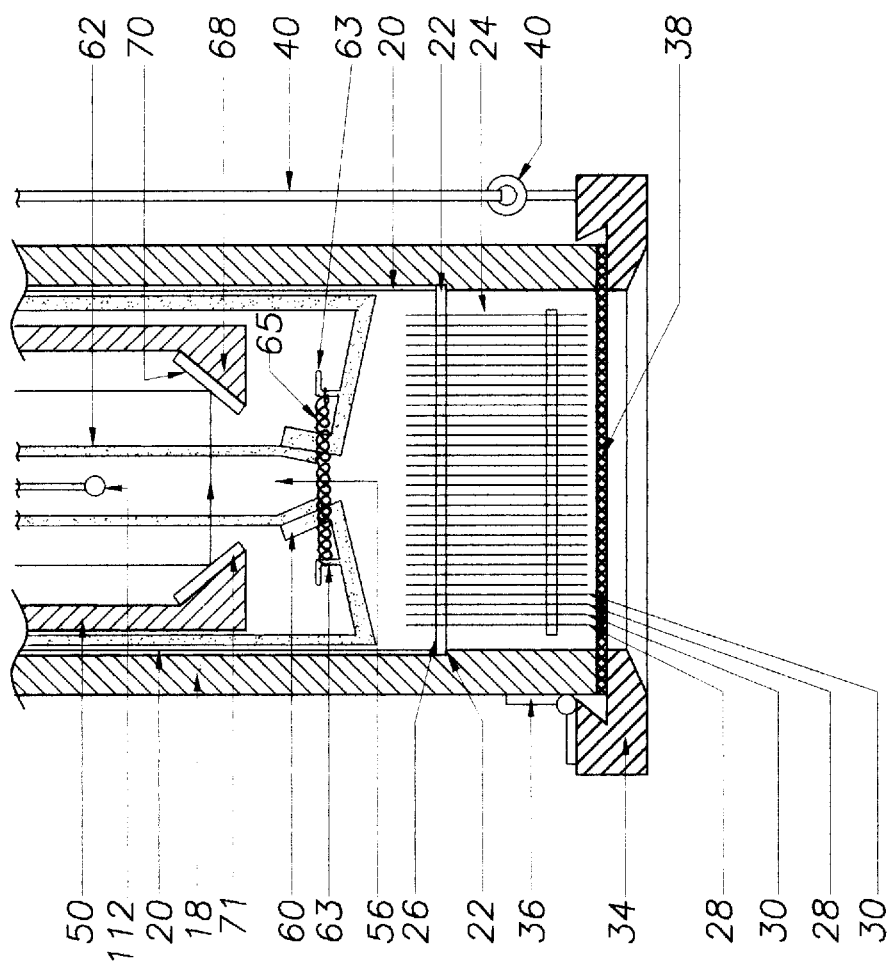
FIG. 5 is an enlarged, broken away cross sectional view, of the lower portion of the sensor of FIG. 4.
Figure 6:
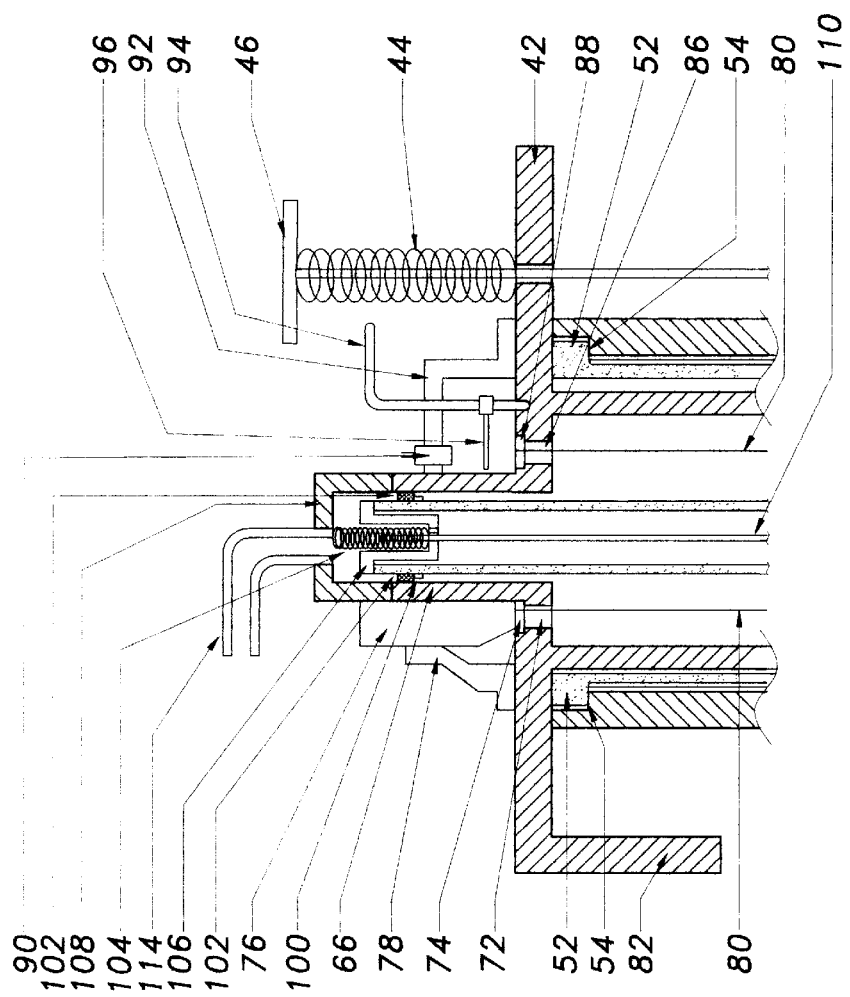
FIG. 6 is an enlarged, broken away cross sectional view of the upper portion of the sensor of FIG. 4.

Referring to FIGS. 4, 5 and 6, the sensor 10 includes an elongate cylindrical housing 18 preferably made of teflon with two narrow grooves 20 extending vertically along the interior surface of the housing and forming shoulders 22 at the bottom thereof. Teflon is preferred over stainless steel for housing 18 because teflon is a poor thermal conductor and hence can be safely handled once removed from the hot oil bath.

A parallel plate capacitor 24 with electrically connected alternate plates is suspended at the bottom of housing 18 with cross beam 26 resting on shoulders 22 at the bottom of grooves 20. Small teflon rings (not shown) are used to electrically insulate the two overlapping stacks of alternating parallel plates 28 and 30 forming capacitor 24. The teflon rings also act to provide equal spacings between the plates. The wires (not shown) for electrical connection to the parallel plates of the capacitor are located in grooves 20. The internal volume of housing 18 is chosen so that the volume of the oil for combined optical transmission and impedance measurements is about 50 ml. The capacitance is measured using a direct current oscillator bridge circuit (not shown) containing parallel plate capacitor 24 operating in the frequency range of about 1 to 10 kHz.

An annular teflon ring 34 is hingedly connected at the bottom of housing 18 by hinge 36 and a thick, replaceable hydrophillic filter 38 is press-fitted between ring 34 and the bottom edge of housing 18, see both FIGS. 4 and 5. A linked rod 40 is connected at one end thereof to ring 34 on the opposite side to hinge 36. The other end of the rod passes through an annular top plate 42 located at the top end of housing 18. Rod 40 passes through a spring 44 above plate 42 and is attached at the upper end to a pushbutton 46. The spring 44 resiliently biases pushbutton 46 upwards to maintain ring 34 and filter 38 tightly against the bottom edge of housing 18 to prevent leakage around the edges. Pressing down on pushbutton 46 causes annular ring 34 to pivot downwardly about hinge 36 so that filter 38 may be replaced.

A shaped pyrex glass cup 50 fits inside housing 18 and is supported at the top thereof by lip 52 resting on shoulder 54.

There is enough clearance provided between glass cup 50 and housing 18 to accommodate the difference in thermal expansion between the teflon and the glass. Located at the bottom of glass cup 50 is a concentric hole 56 bounded by a ground conical glass joint 60. The conical bottom end of a open pyrex glass tube 62 fits into the ground glass joint 60 to provide an air tight seal. The bottom portion of the glass cup 50 is provided with concentric hooks 63 to hold a coiled heating element 65 with power lines in groove 20.

Referring to both FIGS. 4 and 6, top plate 42 is fabricated of teflon and covers the top portion of housing 18. A cylindrical tube 66 integrally formed with plate 42 provides a recess into which the top end of glass tube 62 is inserted. There are two diametrically opposed projecting members 68 extending downwardly into housing 18 from plate 42 that support two small opposed mirrors 70 and 71 (FIGS. 4 and 5) at a 45° inclination from the vertical. There is a first recessed hole 72 in plate 42 to receive a transparent glass plate 74. A diode laser unit 76 is mounted within a light tight enclosure 78 to project a laser beam along an optical path shown by line 80 through the interior of housing 18. Top plate 42 is L-shaped having a downwardly projecting arm 82 used to hook side wall 14 of fryer 12, see FIG. 3.

Top plate 42 includes a second recessed hole 86 diametrically opposed to first hole 72 and a glass plate 88 located in the recessed hole. A photodiode detector 90 enclosed in a light tight enclosure 92 is located in the optical path to receive the laser beam reflected off mirror 70. Light tight enclosures 78 and 92 prevent ambient light entering optical path 80 of the sensor. A handle 94 is rotatable mounted on plate 42 and has a colored glass plate 96 attached thereto which is used as a reference for calibration of the optical system. The handle 94 is used to rotate reference glass plate 96 into the optical path for calibration and out of the optical path when in use.

Glass tube 62 is provided with a circumferential lip 100 located within tube 66 to support a spongy ring 102 made of suitable stuffing materials which prevent the entry of oil fumes and smoke into the optical path on the exterior of tube 62 but within housing 18. A cup-shaped perforated teflon stopper 106 is inserted into the upper end of tube 62. A spring 104 located in stopper 106 bears against an annular end plate 108 of tube 66. A teflon rod 110 attached to the bottom of stopper 106 extends downwardly into tube 62 and is provided with a thermocouple 112 (FIGS. 4 and 5) at the bottom end thereof for monitoring the temperature within tube 62. It will be understood that other standard temperature probes may be used besides thermocouple, including thermistors or resistance temperature detectors (RTD). An L-shaped exhaust tube 114 is attached to annular top plate 108 to provide an exhaust passageway for oil fumes while preventing entry of ambient light into the optical path. Holes and passageways for electrical connections and other supplementary mechanical utilities are conveniently provided, wherever necessary.

Referring again to FIG. 3, a handle 120 is attached to top plate 42 for moving sensor 10. The laser diode unit 76 used in the present apparatus is a 0.8 mW, 675 nm Kaken SMART²™ brand diode laser module, InterTAN Canada Ltd., Barrie, Ontario, Canada. It will be understood to those skilled in the art that other laser diodes or light sources may optionally be used.

The oil quality sensor 10 forming part of the subject invention is includes microprocessor 16 (FIG. 3) to coordinate simultaneous measurement of capacitance, temperature and transmittance and to manipulate the data to obtain the information for assessing the oil quality. The details of the electronic circuits for the capacitance, temperature sensor and are not discussed herein as those skilled in the art will understand how to connect the components of sensor 10 with the microprocessor 16.

Figure 7:
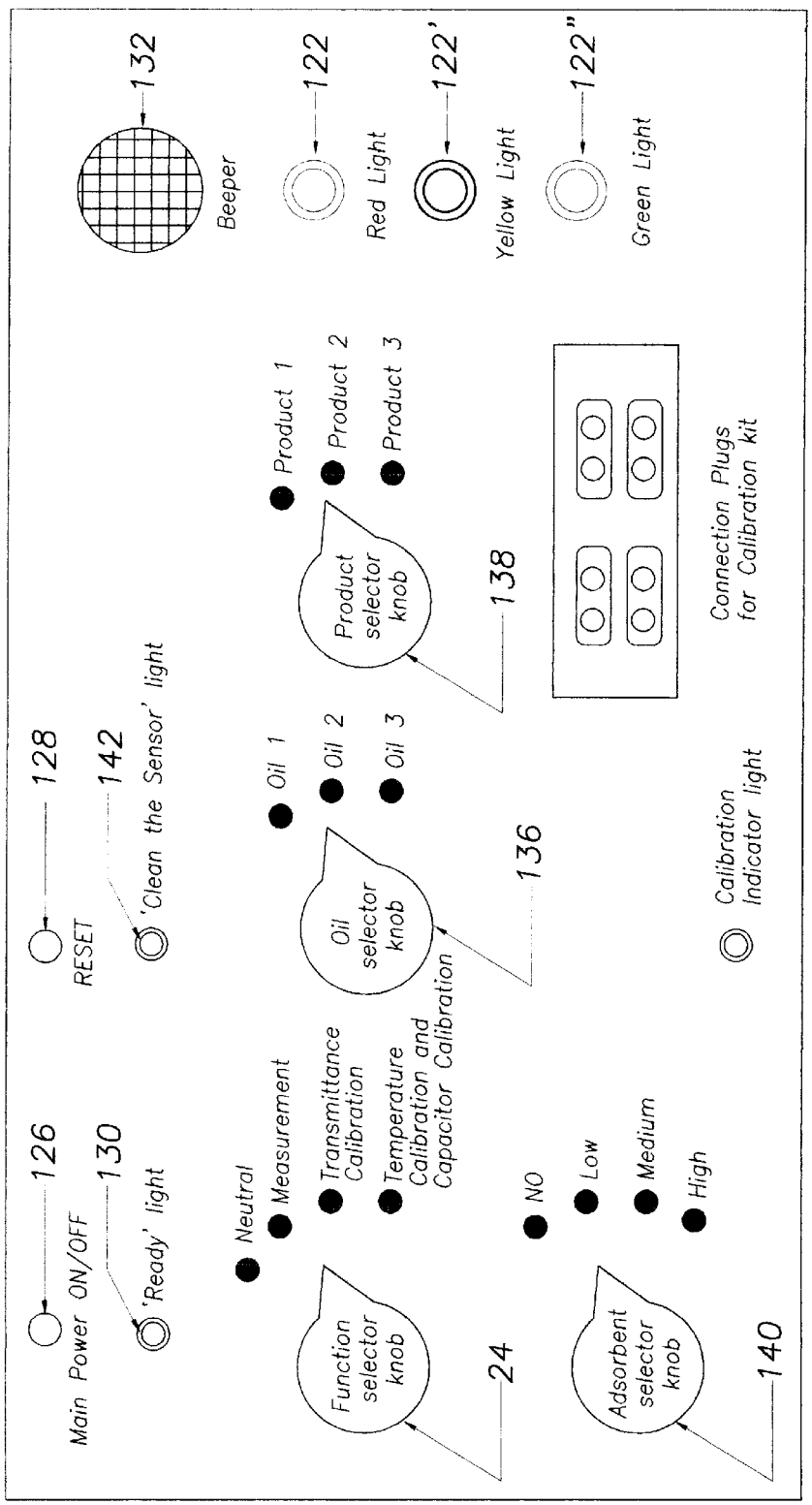
FIG. 7 is diagram of an example control board used with a microprocessor and the sensor of FIG. 4.

FIG. 7 illustrates a schematic layout of an example control board of the microprocessor showing sensor control switches 124, 136, 138 and 140 and various reset switches and other indicator light. The sensor includes a red indicator light 122 for indicating "definitely bad" oil; a green indicator light 122" for "definitely safe" oil; and a yellow light 122' for "maybe good, maybe bad" oil. An indicator light 142 indicates the sensor should be cleaned. This scheme is especially suitable in busy restaurants, as the operator can plan changing the oil in advance or replenish just enough to get through the day's operation.

Oil selector switch 136 is for accessing the stored value of the capacitance of the various pure oils used for the different cooking applications. Food product selection switch 138 and adsorbent selector switch 140 are for accessing MSPT values correlated with food product and absorbents.

Figure 8A:
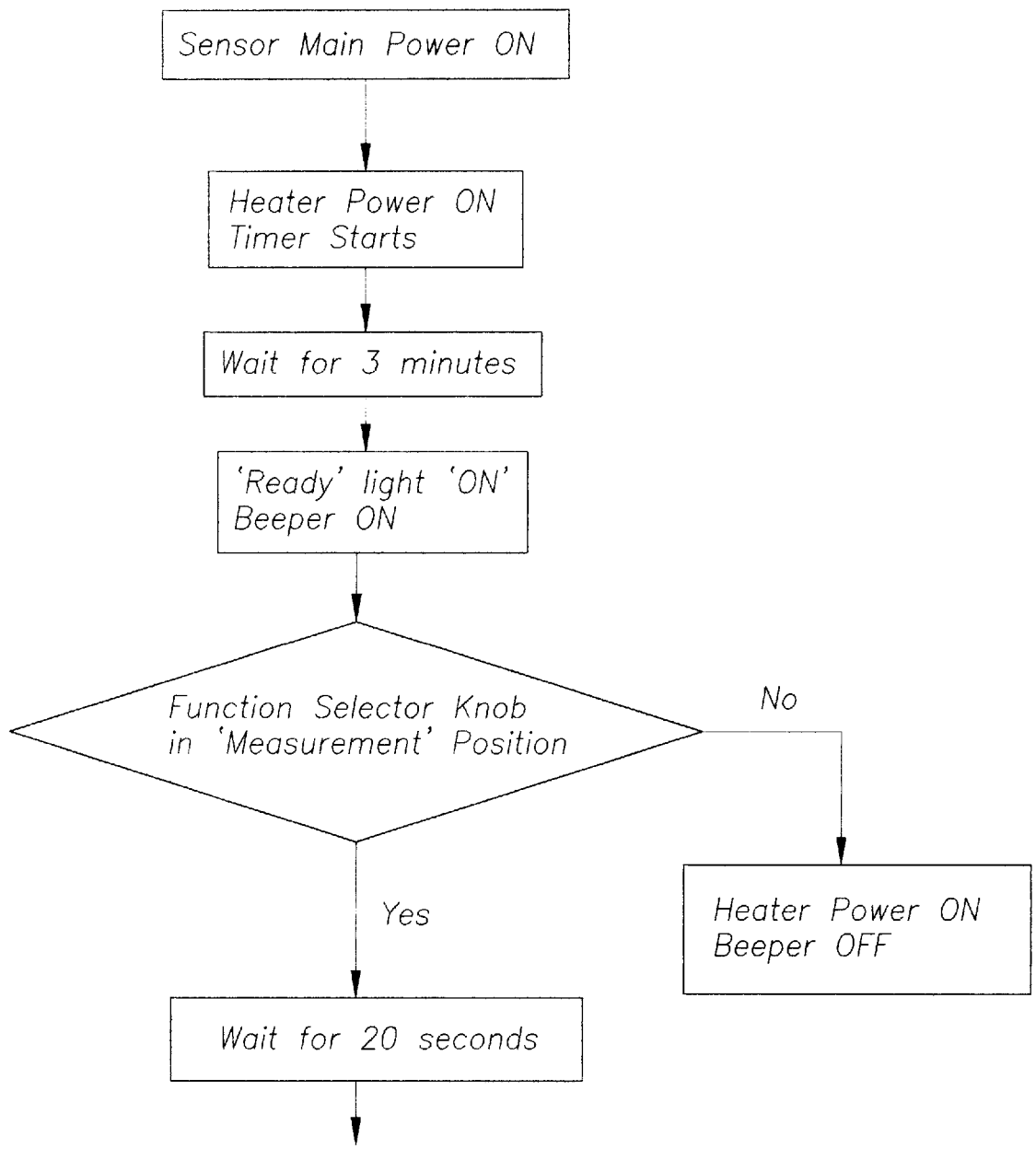
FIGS. 8(a) and 8(b) show a flowchart of an example sensor initiation program.
Figure 8B:
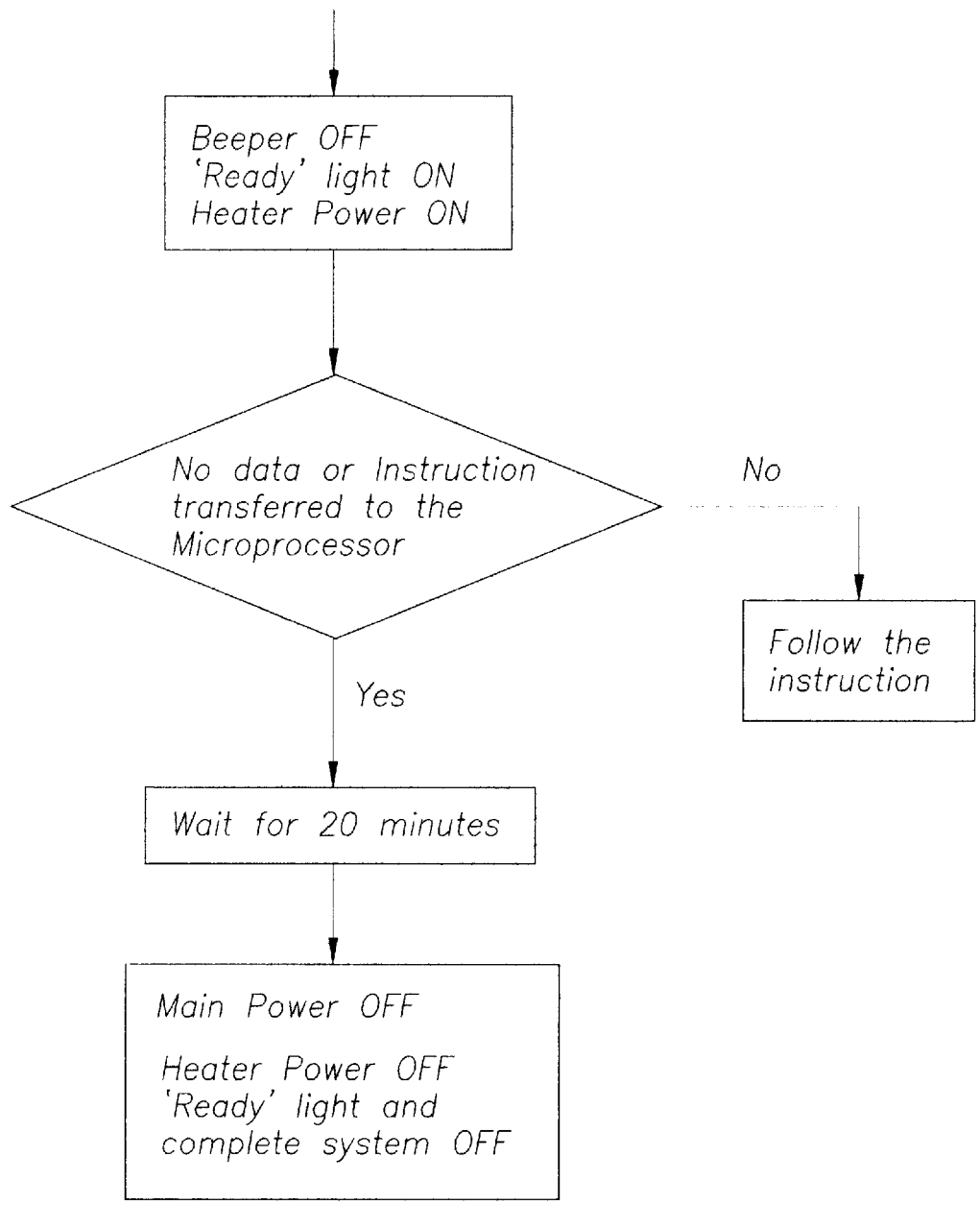

The following description of the operation of the sensor is meant to be non-limiting. Referring to FIGS. 4 and 7, with sensor removed from cooker 12, pushbutton 46 is depressed to pivot annular ring 34 to an open position to drain oil from housing 18 and a fresh filter 38 is inserted into ring 34 and pushbutton 46 is released to pivot ring 34 closed. Next, the main external power supply to the sensor is switched ON and reset button 128 of microprocessor 16 (FIG. 3) is activated. This activates the microprocessor to start a timer and turn on the power supply to the heating coil in the glass cup 50. The glass cup 50 is heated to about 150° C. to avoid breakage when the hot frying oil comes in contact with the glass. The red, yellow and green indicator lights will be off at this stage. After about 3 minutes of heating, the microprocessor will switch on 'ready' light 130 and beeper 132. The beeper 132 will stop after 20 seconds, but the 'ready' light 130 remains ON for 15 minutes, after which the microprocessor and all the power supplies turn off for safety, if not being used. A sample of a non-limiting flow diagram of a microprocessor program for initializing the sensor is shown in FIGS. 8(a) and 8(b) wherein the flow diagram of FIG. 8(b) is a continuation of the flow diagram of FIG. 8(a).

Referring to FIG. 7, once the 'ready' light 130 is ON, the sensor is ready for measurements and the function selector knob 124 is switched to 'measurement' position. The oil selector knob 136, the product selector knob 138 and the adsorbent selector knob 140 are each set to identify the correct combination and create the corresponding address. The microprocessor reads the data from the product and adsorbent selector knobs, 138 and 140 respectively, when function selector knob 124 is in the measurement position. The microprocessor uses this address to recall the correct $Cn^*_{pure}$, $\Delta C^*_{low}$, $\Delta Cn^*_{high}$, $MSPT_n^*$ and the temperature dependence equations for capacitance and transmittance for the combination of oil, product and absorbent from the EAPROM such as shown in Table 1.

Referring to FIG. 3, sensor 10 is then immersed into the oil 130 in fryer 12 by hanging it from the fryer wall 14. Referring to FIG. 4, due to the hydrostatic pressure difference, the oil flows into the interior of housing 18 through hydrophillic filter 38 which removes the suspended particles as well as the moisture present in the oil. The oil rises all the way into the glass tube 62 up past the temperature sensor 112. The oil measurements are made well below the surface of the oil in the cooker and shielded by the housing to prevent spurious readings due to drafts and the like.

Figure 9A:
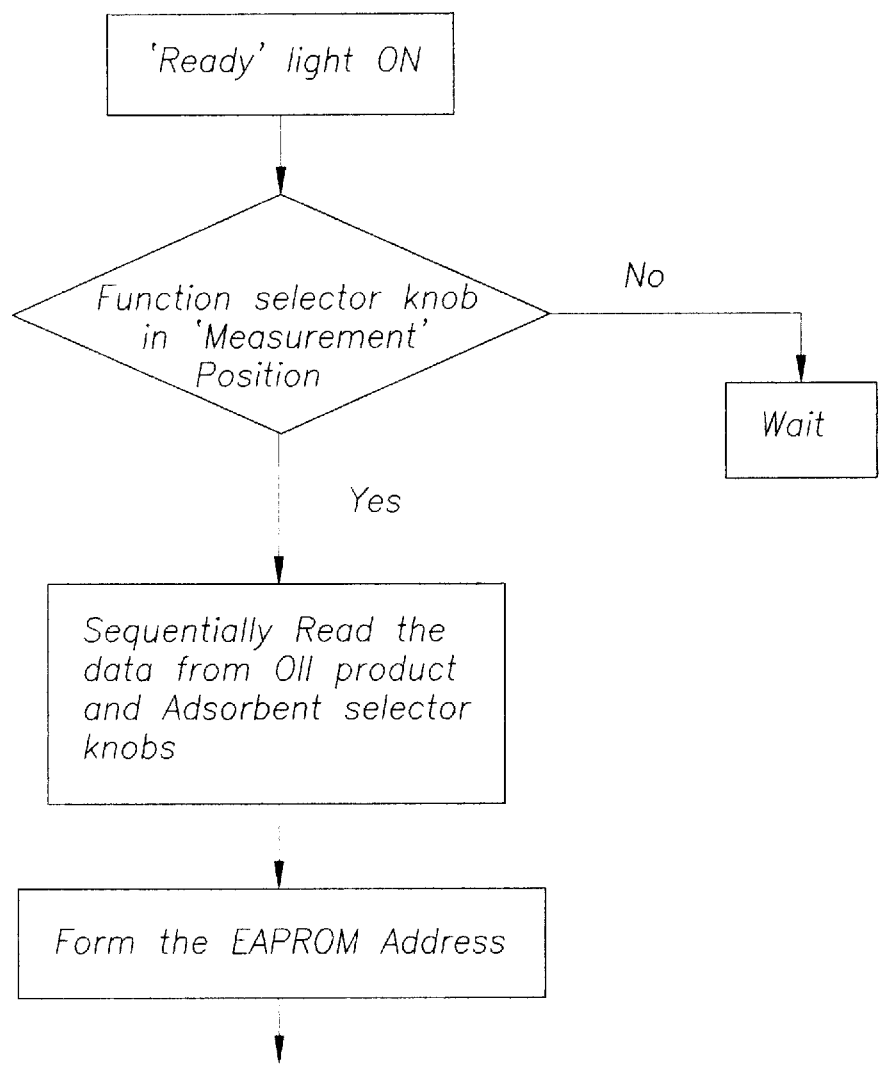
FIGS. 9(a) to 9(e) show a flowchart of a sample microprocessor program for measurement of oil quality in accordance with the present invention.
Figure 9B:
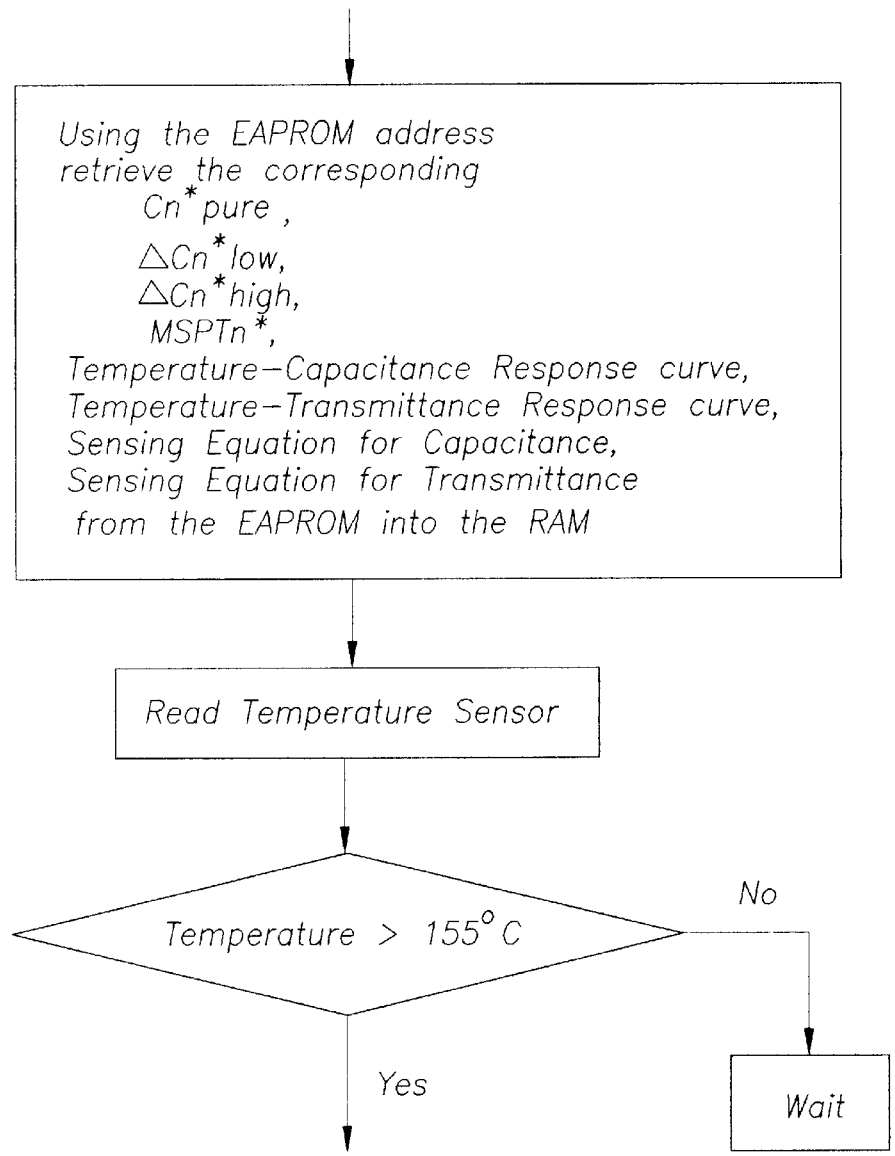
Figure 9C:
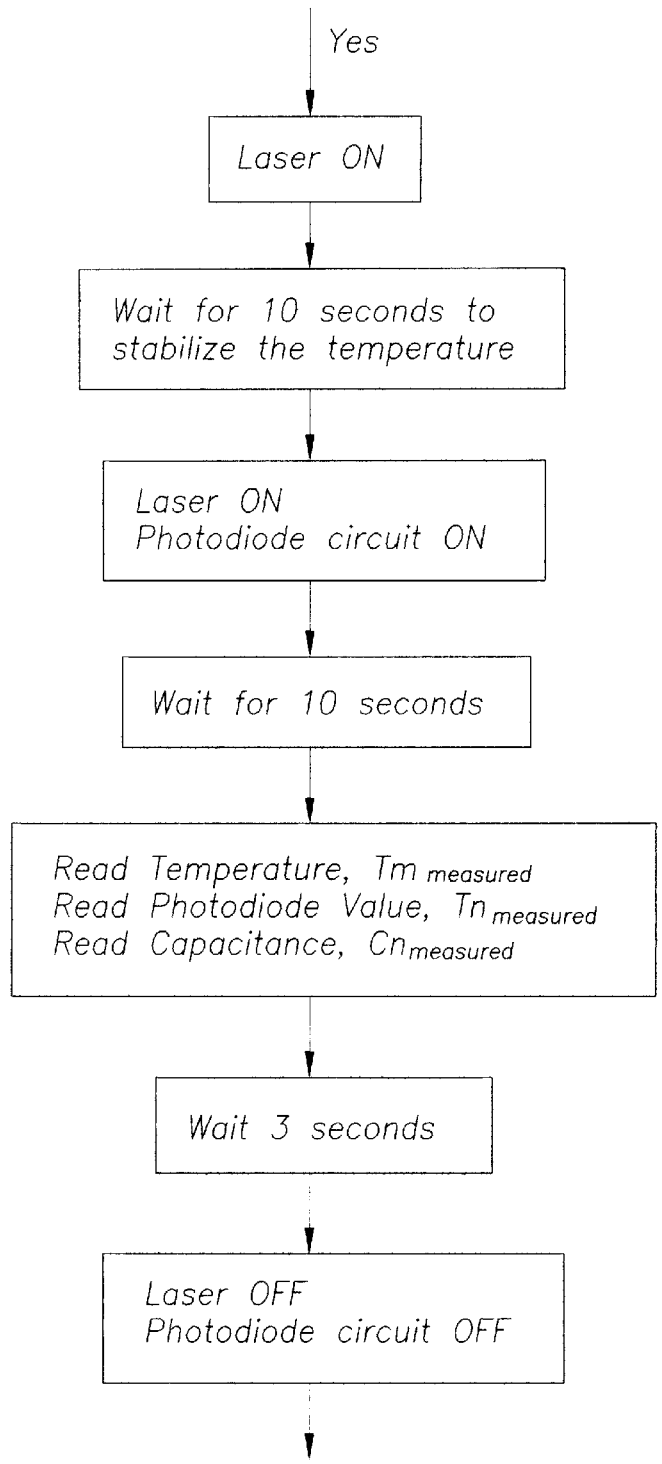
Figure 9D:
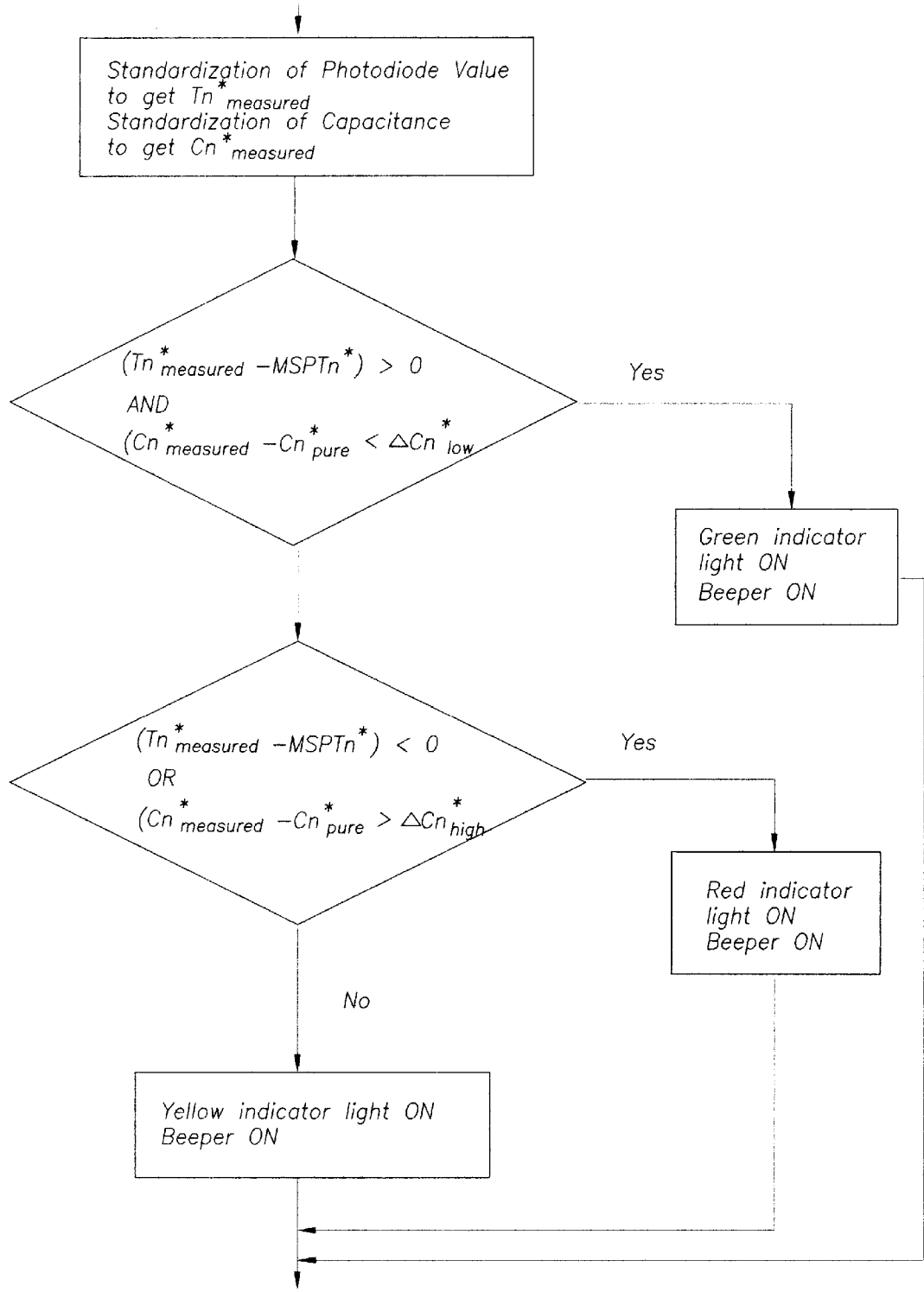
Figure 9E:
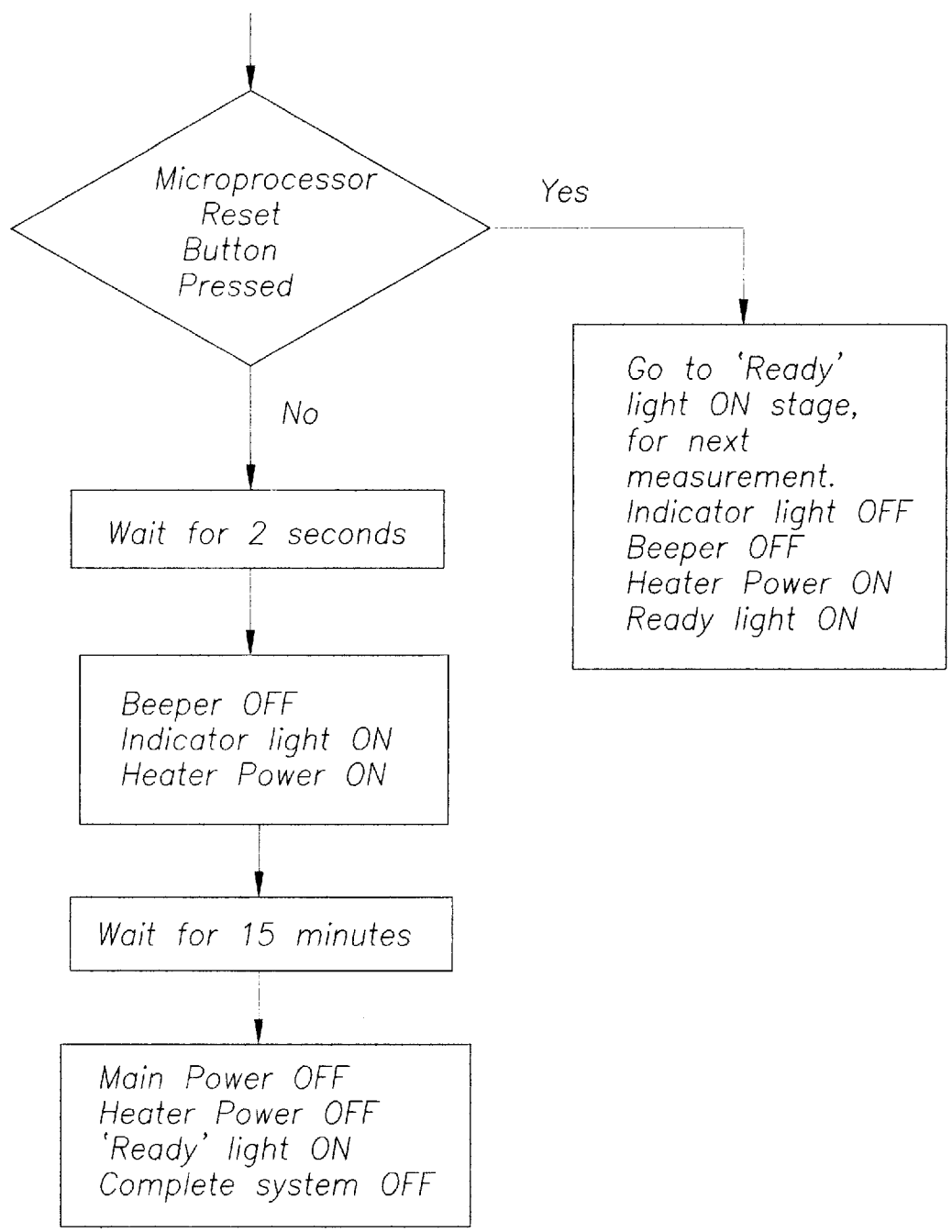

FIGS. 9(a) to 9(e) provide a flow diagram of an example microprocessor program for the above described measurements wherein FIG. 9(b) is a continuation of the flow diagram of FIG. 9(a), FIG. 9(c) is a continuation of FIG. 9(b), FIG. 9(d) is a continuation of FIG. 9(c) and FIG. 9(e) is a continuation of FIG. 9(d). The controlling software is programmed so that the microprocessor acts on the temperature reading only if it is above about 155° C., which is the lower limit of the frying temperature range. The temperature sensor 112 will show a temperature above 160° C. only by the direct contact with the oil. Therefore, temperature sensor 112 acts also as an oil level indicator, to make sure that the oil rises above mirrors 70 in optical path 80. Once the microprocessor reads a temperature above 155° C. it turns laser 76 and photodiode detector 90 circuits ON and waits for 10 more seconds to stabilize the temperature of the oil and the photodiode readings. After 10 seconds the microprocessor reads the temperature, the capacitance $Cn^*_{measured}$, and the transmittance $Tn^*_{measured}$, simultaneously. The laser and photodiode circuits are turned off 3 seconds after reading the data. The values of the capacitance and the transmittance are standardized as previously described to obtain the corresponding $Cn^*_{measured}$ and $Tn^*_{measured}$ which are stored in the RAM of the microprocessor. Then, the values of $Cn^*_{measured}$, $Cn^*_{pure}$, $\Delta Cn^*_{low}$, $\Delta Cn^*_{high}$, $Tn^*_{measured}$ and $MSPTn^*$ for the combination addressed by the selector knobs are recalled into the sensing equations to make the logical decisions as described below:

1. The red indicator light 122 is ON to indicate "definitely bad" oil if, $$(Tn^*_{measured}-MSPTn^*)<0$$

OR $$(Cn^*_{measured}-Cn^*_{pure})>\Delta Cn^*_{high}$$

2. The green indicator light 122' is ON to indicate "definitely good" oil if, $$(Tn^*_{measured}-MSPTn^*)>0$$

AND $$(Cn^*_{measured}-Cn^*_{pure})<\Delta Cn^*_{low}$$

3. The yellow indicator light 122' is ON for all the conditions of sensing other than red and green.

The microprocessor may be programmed to turn the sensor system OFF if no more measurements are performed within a preset period of time.

The capacitance measurement of the present device has been found to provide a more reliable measure of the dielectric properties of the oil as compared to known devices. This is due in part to the use in the present invention of the capacitor comprising a plurality of larger surface area, parallel plates than used in known devices. Further, the volume of oil sampled in known devices for measuring dielectric constant is approximately 1 mL while the volume of oil sampled in the capacitance measurement using the present invention herein is up to about 25 mL.

Calibration of the Sensor

Figure 10:
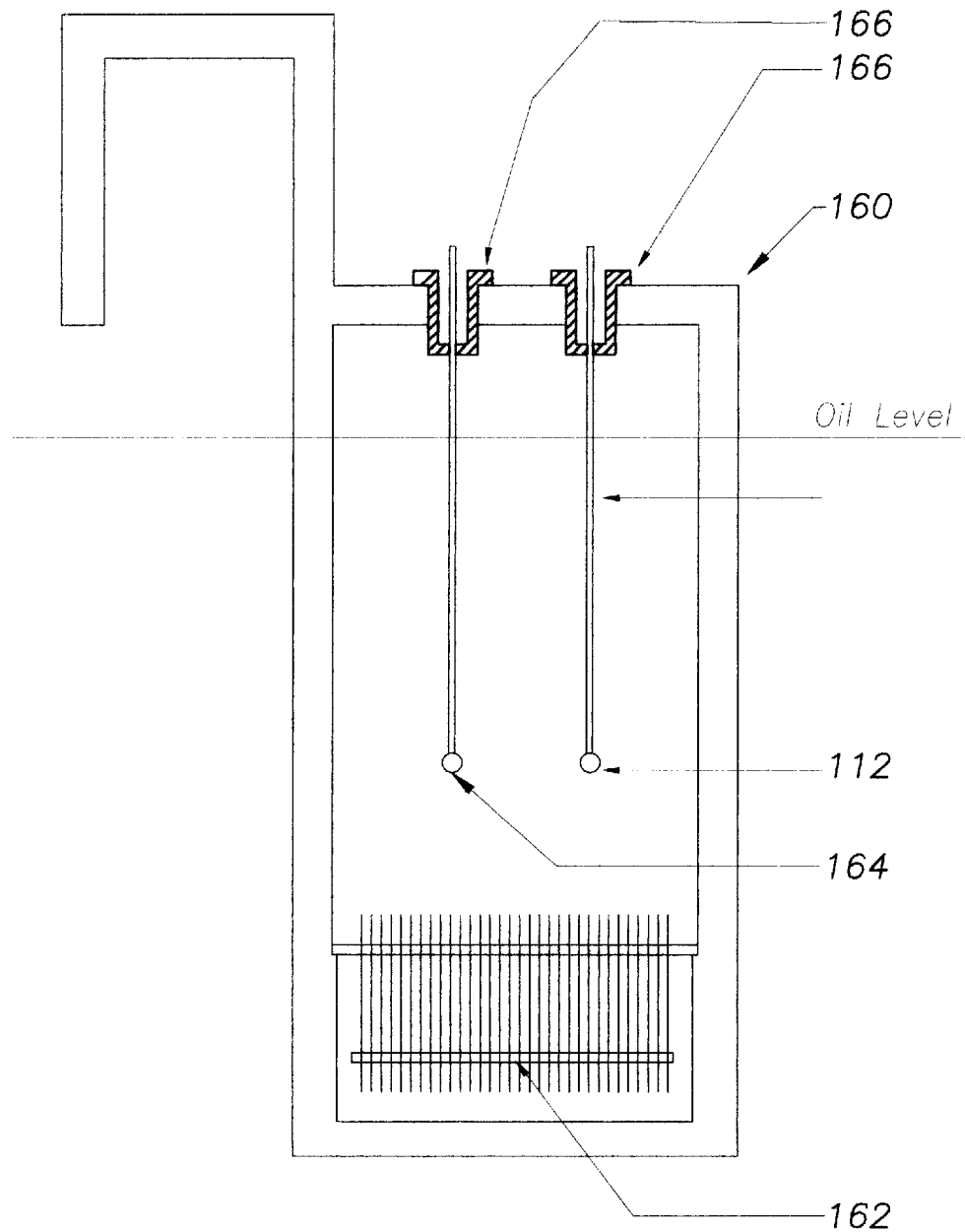
FIG. 10 is a cross section of a calibration cell for calibrating the sensor of FIG. 4.

The calibration of sensor 10 includes the recalibration of temperature probe 112, parallel plate capacitor 24 and the optical circuit. FIG. 10 is a diagram of a calibration cell 160 which may be used to calibrate both temperature probe 112 and the parallel plate capacitor 24 in sensor 10 of FIG. 4.

Cell 160 supports a parallel plate capacitor 162 essentially identical to parallel plate capacitor 24. Cell 160 supports a temperature sensor 164 substantially identical to probe 112 with both being suspended from teflon cups 166. Capacitor 162 and temperature sensor 164 in calibration cell 160 act as the references for calibration. The electrical connections to reference capacitor 162 and temperature probe 164 are provided from the respective circuits used with oil sensor 10.

Referring again to FIG. 7, when the function selector knob 124 of sensor 10 is in the 'measurement' position as shown, the microprocessor is programmed to read the data only from sensor 10, and not from calibration cell 160. When the function selector knob is turned to one of the 'calibration' positions, the microprocessor is programmed to read the data intermittently from both sensor 10 and calibration cell 160 to avoid duplication of electronic circuits for the measurements.

Figure 11A:
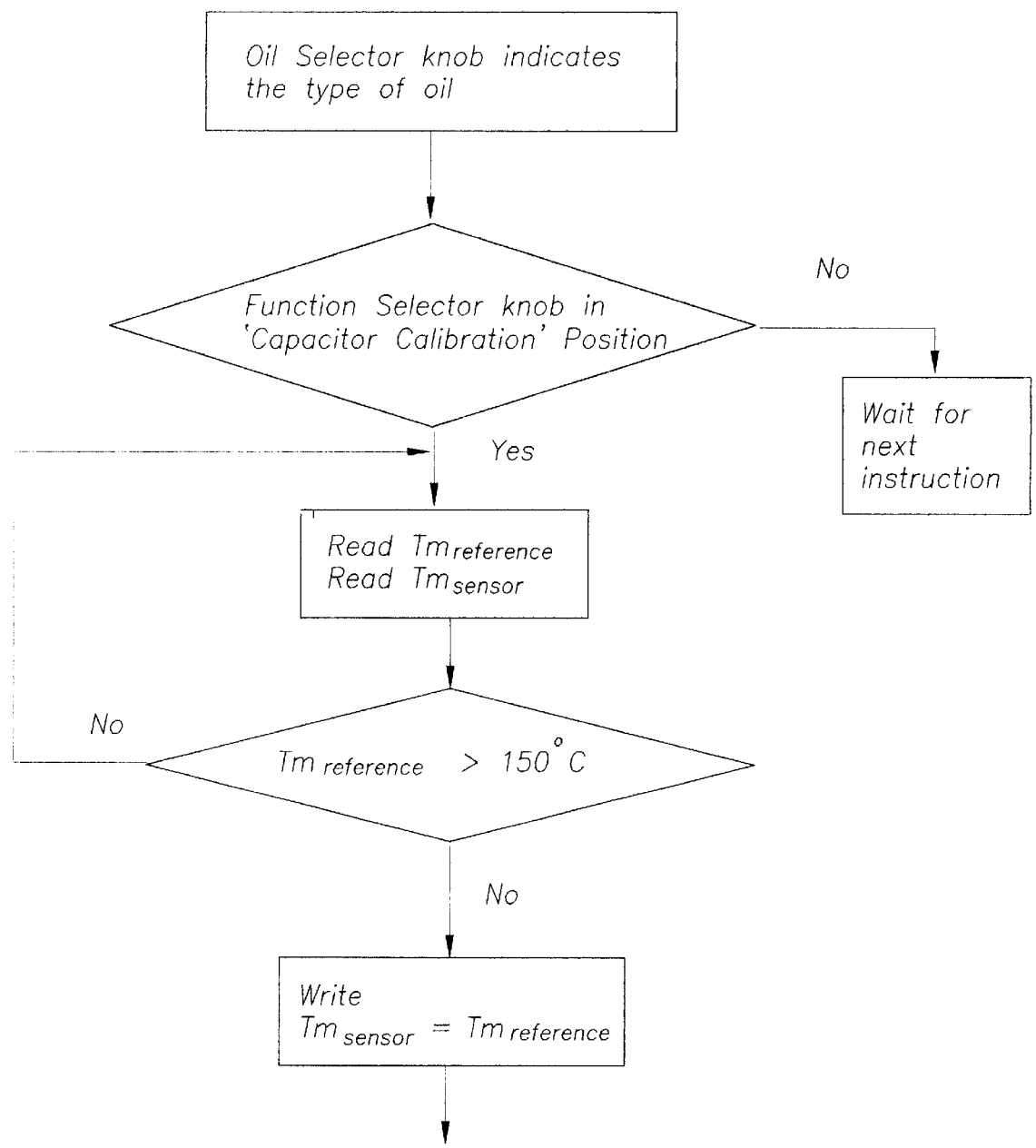
FIGS. 11(a) to 11(c) show a flowchart of an example microprocessor program for calibration of the temperature probe and capacitor in the sensor of FIG. 4.
Figure 11B:
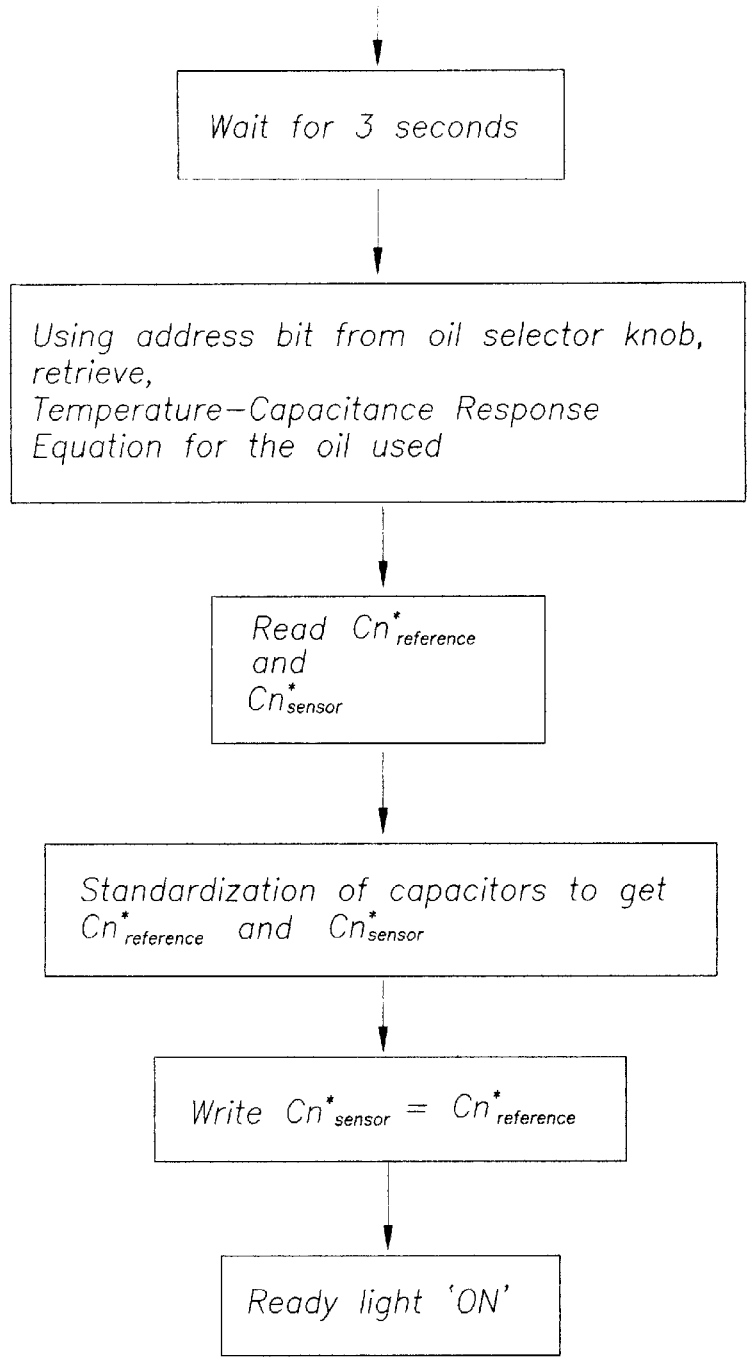

The flow diagram of an example microprocessor program for the calibration of capacitor 24 and temperature probe 112 shown in FIGS. 11(a) and 11(b), wherein FIG. 11(b) is a continuation of the flow diagram of FIG. 11(a). $Tm_{reference}$ is the temperature measured by reference temperature sensor 164 and $Tm_{sensor}$ is the temperature measured by sensor 112. The function selector knob 124 is turned to the 'temperature calibration and capacitor calibration' position. The microprocessor reads the data intermittently from the temperature sensors 112 and 164 at an optimum rate. When $Tm_{reference}>150°$ C., the software is programmed to re-write ($Tm_{sensor}=Tm_{reference}$), into the EAPROM. The software makes the necessary corrections to read $Tm_{sensor}$ equal to $Tm_{reference}$ until the next calibration is performed. $Tm_{sensor}$ and the $Tm_{reference}$ will numerically be equal. Thus, the temperature sensor 112 of device 10 is first calibrated against reference temperature sensor 164 in the calibration shown in FIG. 10. The microprocessor waits for 3 seconds to stabilize the system. The appropriate temperature-capacitance response equation for the oil is recalled using the address bit from the oil selector knob 136. The microprocessor reads the data ($Cn_{reference}$ and $Cn_{sensor}$) from the capacitors 162 and 24 and the capacitance values are standardized to obtain $Cn^*_{reference}$ and $Cn^*_{sensor}$. The software re-writes ($Cn^*_{sensor}=Cn^*_{reference}$) into the EAPROM. The $Cn^*_{reference}$ will numerically be equal to $Cn^*_{reference}$ until the next calibration is performed. In this way capacitor 24 is calibrated against reference capacitor 162 in the calibration cell (FIG. 10) and the 'ready' light 130 turns 'ON'.

Figure 11C:
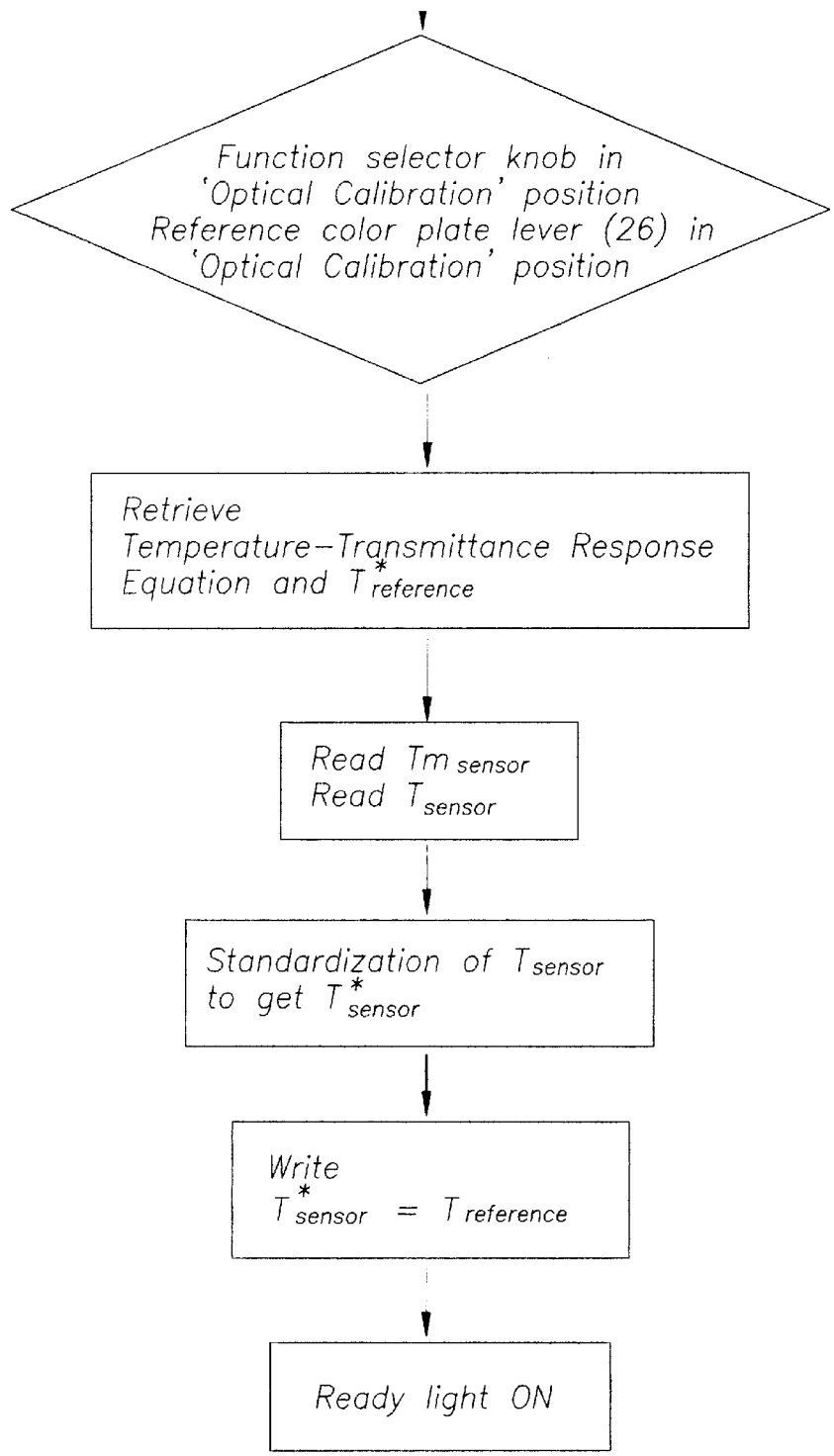

FIG. 11(c) provides a flow diagram of a sample microprocessor program for the optical calibration. Referring to FIG. 4, lever 94 is rotated to bring glass plate 96 of the reference color into the optical path. The laser beam can reach the photodiode 90 by passing through the reference color plate 96. $T_{reference}$ is the transmittance received at photodiode 90 when the optical path is in its cleanest state with the laser passing through reference plate 96. The standardized $T^*_{reference}$, corrected to the standard temperature of measurement, is stored in the EAPROM of the microprocessor as the reference for optical calibration.

The MSPT of each oil is estimated assuming that the optical path is in its cleanest state. But, in practice, the transparency of all the glass components in the optical system can be affected with use due to various factors such as deposition of oil fumes, smoke, dust, etc. The intensity of the laser and the sensitivity of the photodiode circuit also can vary significantly with long use. Therefore, the optical system preferably should be calibrated depending on usage. One sample of an optical calibration procedure is now described.

With sensor 10 cleaned, lever 94 is moved to the 'calibration' position to bring reference glass plate 96 into the optical path so that the laser beam impinging on photodetector 90 passes through plate 96. $T_{sensor}$ is denoted as the transmittance received at photodiode 90 after passing through plate 96. The standardized $T^*_{sensor}$ will not be equal to $T^*_{reference}$ possibly due to a number of factors such as unclean optical path, variation in the laser intensity and the like.

The function selector knob 124 is switched to the 'transmittance calibration' position. The microprocessor is programmed to re-write ($T^*_{sensor}=T^*_{reference}$) into the EAPROM. The $T^*_{sensor}$ will numerically be equal to $T^*_{reference}$ until the next calibration is done. The 'ready' light 130 switches 'ON' indicating that the optical circuit is calibrated against the $T^*_{reference}$ stored in the EAPROM. If $T^*_{sensor}$ is too low compared to $T^*_{reference}$, the microprocessor is programmed to turn the 'clean the sensor' light 142 ON, indicating that a cleaning of the components in the optical path is necessary. The function selector knob 124 is switched to the 'measurement' position and plate 96 is rotated from the optical path to continue with regular oil quality measurements.

Detection of Smoke Point

Figure 12A:
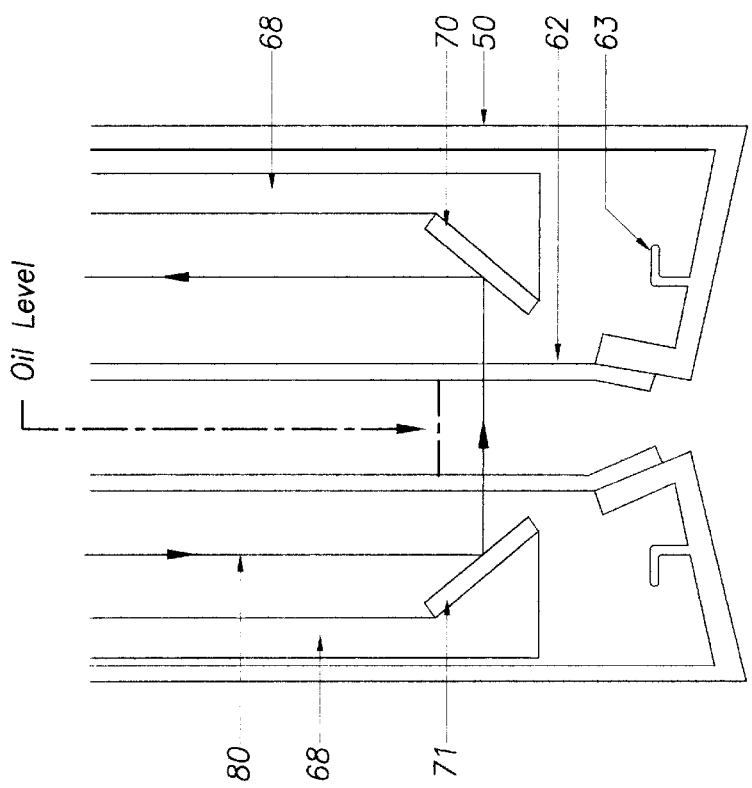
FIG. 12(a) is a cross sectional view, broken away, showing the relative positioning of mirrors in the optical system of the cell of FIG. 4 for measuring transmittance of oil.
Figure 12B:
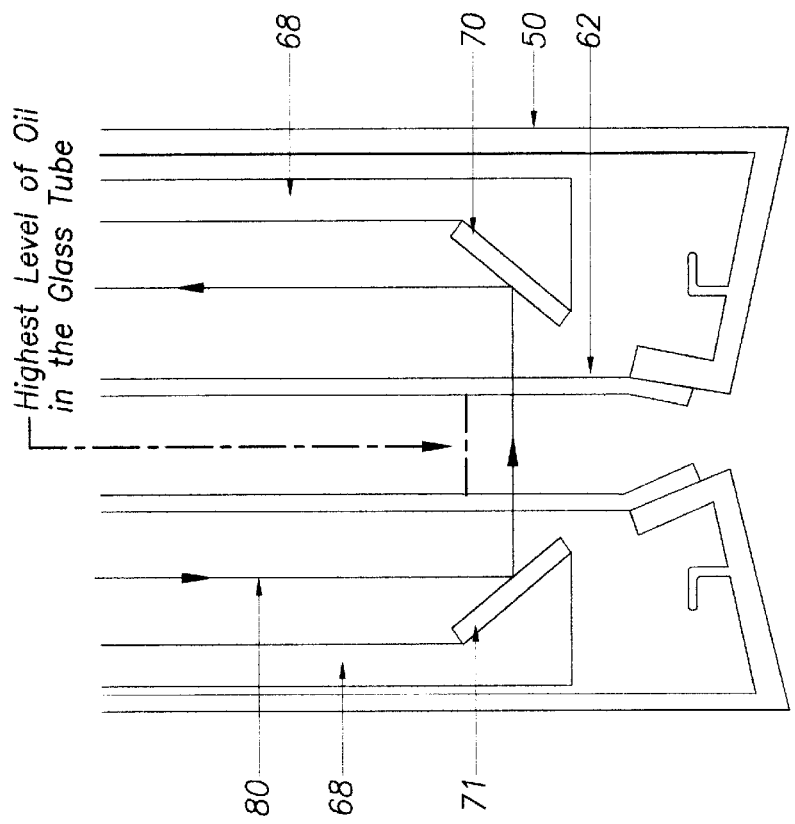
FIG. 12(b) is similar to FIG. 12(a) but shows the relative positioning of mirrors in the optical path of the cell of FIG. 4 for measuring transmittance of smoke.

Before the oil enters glass tube 62, the smoke evolving from the oil surface inside the sensor passes through the optical path between mirrors 70. The microprocessor and the optical circuit may be programmed to measure the change in transmittance due to the smoke column. The reduction in transmittance by the smoke, beyond a pre-set limit indicates that the smoke point of the oil is below 170° C., the frying temperature. This method requires the cleaning of the glass tube 62 before every measurement but this may be avoided by making the pair of mirrors 70 slide vertically upward as a single unit, above the highest level of oil inside tube 62. FIGS. 12(*a*) and 12(*b*) illustrate the relative positioning of mirrors 70 for measuring transmittance of oil (FIG. 12(*a*)) and smoke point (FIG. 12(*b*)). Mirrors 70 can be slid vertically upward using a simple lever mechanism (not shown). When the mirrors are slid up above the oil level O, the optical path passes through the smoke S and the optical circuit measures the smoke point. The sensing expressions will become a function of smoke point also. When the mirrors are slid down, the optical path passes through the oil to measure transmittance of the oil.

The method and apparatus of the present invention is advantageous over known methods of monitoring cooking oil for several reasons. The present method provides a quality assessment based on both the chemical and optical conditions of the oil. It also provides a reasonably accurate indication of oils that could possibly contain higher concentrations of leaching fat. Hence, the overall oil quality assessment is more accurate and reliable than the known methods. The concept of the region of uncertainty in the capacitance determination adds to the reliability of the present technique. The calibration procedure is rapid. Each measurement takes only about 30 seconds. The measurements are performed in the frying temperature range so the sensor can be modified for on-line quality assessment applications. A large sample size of total volume 50 mL is used for the combined optical and capacitance measurement, which adds to the accuracy and reliability of the technique. The sensor collects the oil sample from a depth of about 10 cm in the fryer which minimizes interference from moisture. During use the sensor is immersed in the oil so that convectional currents passing by filter 38 provide excellent sampling of the oil in the fryer. The sensor can be readily adapted to any change in measurement criteria (eg. type of cooking oil, food product) by changing the relevant parameters in software. The sensor can measure the smoke point of the oil also, with a minor modification in the design.

It will be understood that the optical circuit and the parallel plate capacitor of the present invention may be re-arranged in numerous other geometrical configurations to suit special applications. For example, the glass cup 50 and the capacitor 24 may be placed closer together to reduce measurement time, as the oil can rise through the capacitor and the glass tube simultaneously. The hardware and the controls may be separate units connected to the sensor by wires. This configuration avoids the possible damage to electronic circuits if the sensor accidently falls into the fryer. Similarly, the capacitor circuit and the optical circuit may be two discrete units controlled by the microprocessor placed in a remote location. This design may be convenient in a large continuous fryer.

Both the optical path and the capacitor may be provided with separate temperature sensors to increase the accuracy of measurement. Optical fibres may be used in the optical circuit of the sensor for greater flexibility. Discrete fibres or bifurcated fibres can be used to suit the design.

Figure 13:
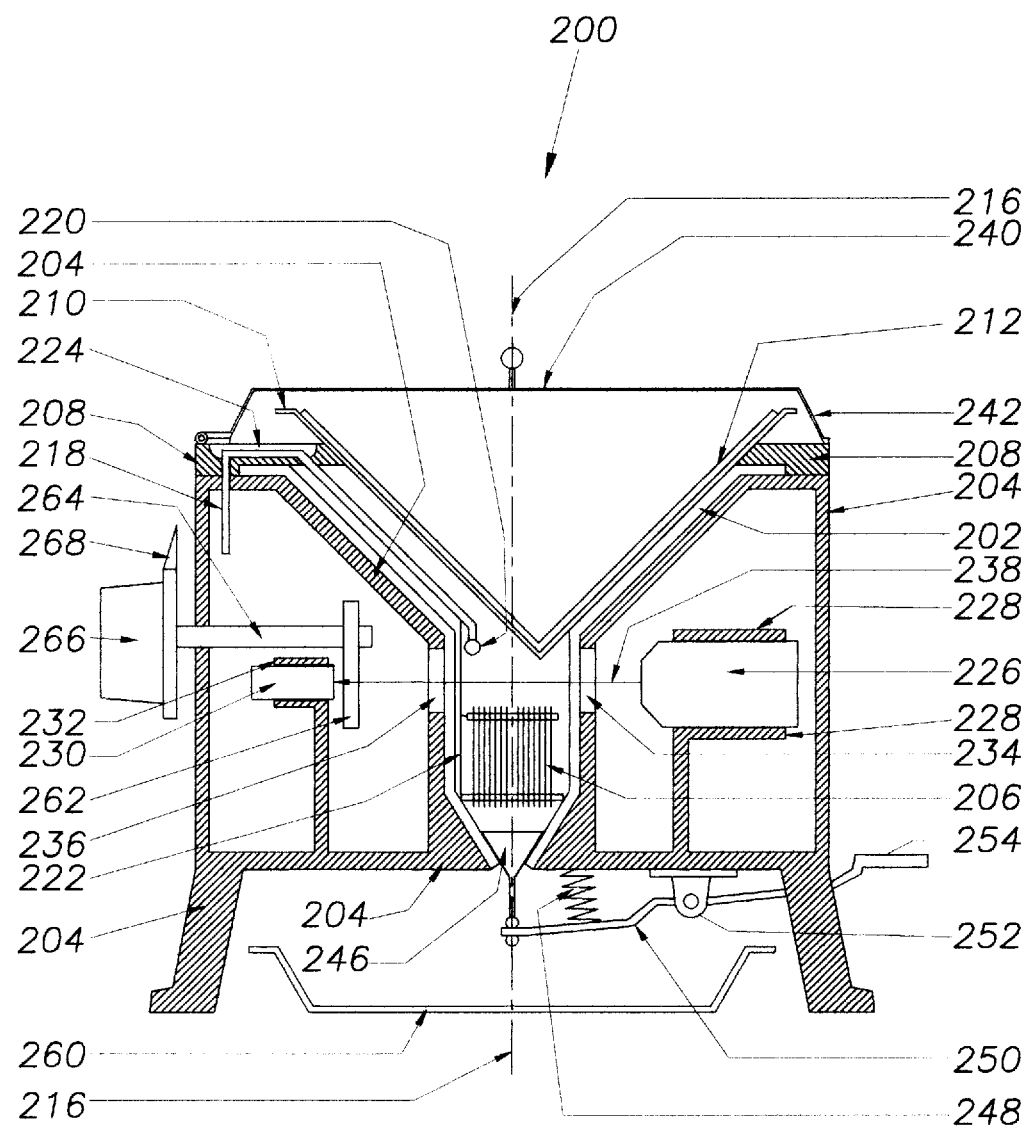
FIG. 13 is a cross sectional view of an alternative embodiment of an oil sensor constructed in accordance with the present invention.

An alternative embodiment of an oil sensor constructed in accordance with the present invention is shown in FIG. 13 generally at 200. Sensor 200 includes a pyrex glass funnel 202 which fits into a housing 204 made of thermoplastic. A parallel plate capacitor 206 comprises a plurality of plates is located inside glass funnel 202. An annular ring 208 is screwed or locked to frame 204 which presses funnel 202 intact against the top of the frame. A perforated funnel 210 made of thermoplastic is supported within glass funnel 202 and in turn supports filter paper 212. Annular ring 208 is provided with a number of holes circumferentially arranged to allow air to freely move out from the gap between perforated funnel 210 and glass funnel 202. The inner hole of annular ring 208 is eccentric with respect to central axis 216. Perforated funnel 210 and filter paper 212 are also placed in eccentric relation with respect to central axis 216.

The gap created between perforated funnel 210 and glass funnel 202 provides access for a bent tube 218 supporting a temperature sensor 220 and associated electrical leads in addition to the electrical leads 222 from capacitor 206. These electrical leads are connected to the sensor electronics hardware for signal processing. A groove 224 on annular ring 208 receives a portion of tube 218 therein for stability. The electronics hardware (not shown) can be placed inside housing 204 or attached to the exterior of the housing as long as appropriate thermal insulation is used. Indicator lights and other controls (not shown) can be placed on the exterior of housing 204.

A laser unit 226 is clamped to a support 228 and a photodiode 230 is clamped to a support 232 in opposing relation to the laser. Two holes 234 and 236 on the interior of housing 204 provide an unobstructed optical path as indicated by arrow 238. Sensor 200 is provided with a hinged cover 240 having small holes 242 along the side below the upper level of perforated funnel 210 to provide free passage of air into and out of the apparatus while preventing the stray light from entering the interior of housing 204. There is a conical shaped teflon valve 246 closing the bottom hole of glass funnel 202. Valve 246 is connected to a lever 250 pivotally connected to housing 204 at pivot point 252 and biased in the closed position by a spring 248 bearing against the housing. Valve 246 is opened by pressing the end portion 254 of lever 250. A small pan 260 placed under valve 246 is for collecting the oil from housing 204.

A reference colour plate 262 for optical re-calibration is attached to a shaft 264 attached in turn to a knob 266 for movement by the operator into or out of the optical path. A pointer 268 on knob 266 indicates the position of the knob for "measurement" and "re-calibration". An oil sample collector for obtaining the required volume of oil from the fryer may be supplied with the sensor.

In operation, the working principles, sensor logic, sensing and calibrating procedures are essentially the same as described with reference to sensor 10 in FIG. 4. In operation, to start the sensing operations, cover 240 is opened and oil to be tested is poured into the housing through filter paper 212 and perforated funnel 210. Cover 240 is closed and the filtered oil flows into the interior of housing 204 containing capacitor 206 to a level above the optical path defined by the laser beam. The eccentricity of perforated funnel 210 with respect to central axis 216 prevents the oil from falling directly on temperature sensor 220 thereby avoiding premature triggering of measurements of capacitance and transmittance. Valve 246 remains closed during the filling and measuring procedures. The oil level rises until temperature sensor 220 is completely immersed. Once the oil immerses the temperature sensor the microprocessor initiates the measurement of transmittance and capacitance as described above with respect to sensor 10.

Portable oil sensor 200 is particularly adapted for home use and may use batteries or a combination of batteries or the house mains. A heater similar to heater coil 65 in FIG. 5 may optionally be employed since the measurement of optical and capacitance is very rapid and the software used can correct for slight temperature drops of the oil during the measurement process.

In order to remove trace oil remaining in housing 204 from previous tests, a sample of the oil to be tested may be first flushed through the sensor housing. A fresh batch of the oil to be tested is then loaded into sensor 200 and the transmittance and capacitance are measured. Subsequent to the determination of oil quality lever 250 is depressed at 252 to open valve 246 thereby draining the oil into pan 260. The oil collected in pan 260 may be discarded if the oil quality is sufficiently poor or otherwise it may be poured back into the fryer from where it was obtained.

Sensor 200 is advantageous for several reasons. The design offers a "table-top" sensor that is not immersed into the oil for cleaner operation as is sensor 10. The amount of teflon is reduced. Valve 246, the insulator spacers for capacitor 206 and tube 218 are the only components made of teflon which reduces the cost of the sensor considerably. Sensor 200 may be readily cleaned by removing and cleaning funnel 210 and replacing filter paper 212. The compact arrangement of capacitor 206, laser 226, detector 230 and temperature sensor 220 allow a rapid measurement of transmittance and capacitance of the small volume of oil so that small leaks through valve 246 are tolerable so long as the oil level does not drop below temperature sensor 216.

Those skilled in the art will understand that the sensor disclosed herein may be used to measure quality of other types of oils including engine oil, transformer oil and the like. The chemical composition of such oils change with usage, causing optical and dielectric changes. Therefore the method and device disclosed herein for monitoring oil quality may be utilized for testing these other oils.

The description of the method and apparatus has been by example only. Those skilled in the art will understand that the algorithms given herein are by example only. Therefore, while the method and apparatus for monitoring quality of cooking/frying oil has been illustrated and described with respect to a preferred embodiments, it will be appreciated by those skilled in the art that numerous variations of the method and apparatus may be made without departing from the scope of the invention.

TABLE 1

Address Formation for EAPROM
Types of Oil → Oil 1 and Oils 2
Types of Food Products → Product 1 and Product 2
Extent of Adsorbent Application → high (1) and low (0)

| Selector knobs of various combinations | | | | EAPROM | | | |
|---|---|---|---|---|---|---|---|
| Oil | Product | Adsorbent | | $Cn^*_{pure}$ | $MSPTn^*$ | $\Delta Cn^*_{low}$ | $\Delta Cn^*_{high}$ |
| 1 | 1 | 0 | → | $C110^*_{pure}$ | $MSPT110^*$ | $\Delta C110^*_{low}$ | $\Delta C110^*_{high}$ |
| 1 | 2 | 1 | → | $C121^*_{pure}$ | $MSPT121^*$ | $\Delta C121^*_{low}$ | $\Delta C121^*_{high}$ |
| 2 | 1 | 0 | → | $C210^*_{pure}$ | $MSPT210^*$ | $\Delta C210^*_{low}$ | $\Delta C210^*_{high}$ |
| 2 | 2 | 1 | → | $C221^*_{pure}$ | $MSPT221^*$ | $\Delta C221^*_{low}$ | $\Delta C221^*_{high}$ |

The microprocessor uses these addresses to recall the corresponding correct $Cn^*_{pure}$ and $MSPTn^*$ from the EAPROM.

Therefore what is claimed is:

1. A device for monitoring change of quality of oils, comprising:
   a) a housing defining a chamber and an opening for access to the chamber, to be inserted into a cooking/frying vat containing cooking oil so that cooking oil enters said opening and substantially fills said chamber;
   b) a parallel plate capacitor located in the chamber which is adapted to provide an output;
   c) means located in said chamber for measuring transmittance of oils which is adapted to provide an output;
   d) means located in said chamber for measuring the temperature of oils which is adapted to provide an output; and
   e) a microprocessor connected to and adapted to store outputs from said capacitor, the transmittance measuring means and the temperature sensing means, said microprocessor calculates transmittance and capacitance values of said oil and compares the calculated transmittance value to a threshold transmittance value for said oil, and compares said calculated capacitance value to a reference capacitance value and relates changes to an increase in the amount of polar molecular constituents of the oil, and wherein said microprocessor utilizes the changes in the capacitance and transmittance values using a correlation algorithm to provide an output indicative of the quality of the oil.

2. The device according to claim 1 wherein said housing includes a filter across said opening for filtering the oil entering said chamber.

3. The device according to claim 2 wherein said housing includes an elongate section enclosing said chamber and a closure member hingedly attached to said elongate section to an end portion thereof and operably coupled to a lever, said closure member defining said opening, said filter being releasably attached to said closure member.

4. The device according to claim 3 wherein said parallel plate capacitor is located in said chamber adjacent to said opening.

5. The device according to claim 4 wherein said housing is fabricated of teflon.

6. The device according to claim 1 wherein said means for measuring temperature protrudes into said chamber and is selected from the group consisting of a thermocouple, thermistor and resistance temperature detectors.

7. The device according to claim 1 wherein the transmittance is measured at a wavelength of about 675 nm using a laser beam.

8. The device according to claim 1 including adjustment means for adjusting the optical path length so that the laser beam passes through oil fumes above an oil level of the oil in said housing for measuring smoke point of said oil.

9. The method according to claim 1 wherein said correlation algorithm provides an output indicating the oil is safe to use if the transmittance is greater than the threshold transmittance value, and the change in capacitance is less than the preselected value.

10. The method according to claim 1 wherein said threshold transmittance is a minimum safe percent transmittance value which is calculated for the type of oil being used and the food being cooked, so that the visual appearance (color) of the fried food has good acceptability.

* * * * *